United States Patent
Kazic et al.

(10) Patent No.: US 10,080,908 B2
(45) Date of Patent: Sep. 25, 2018

(54) LASER SYSTEM AND LASER TREATMENT HEAD THEREFOR

(71) Applicant: Fotona d.o.o., Ljubljana (SI)

(72) Inventors: Marko Kazic, Dob (SI); Matjaz Lukac, Ljubljana (SI)

(73) Assignee: Fotona d.o.o., Ljubljana (SI)

( * ) Notice: Subject to any disclaimer, the term of this patent is extended or adjusted under 35 U.S.C. 154(b) by 131 days.

(21) Appl. No.: 14/743,917

(22) Filed: Jun. 18, 2015

(65) Prior Publication Data

US 2015/0367142 A1 Dec. 24, 2015

(30) Foreign Application Priority Data

Jun. 18, 2014 (EP) .................................. 14002094

(51) Int. Cl.
*A61N 5/06* (2006.01)
*A61B 18/20* (2006.01)
(Continued)

(52) U.S. Cl.
CPC ............ *A61N 5/0603* (2013.01); *A61B 18/20* (2013.01); *A61N 5/0625* (2013.01);
(Continued)

(58) Field of Classification Search
CPC ....................... A61N 5/0603; A61N 2005/063
(Continued)

(56) References Cited

U.S. PATENT DOCUMENTS

| 6,501,551 B1* | 12/2002 | Tearney ............. A61B 1/00096 356/477 |
| 8,709,057 B2 | 4/2014 | Tettamanti et al. |
| 2007/0112343 A1 | 5/2007 | Mische et al. |

FOREIGN PATENT DOCUMENTS

| WO | 2008/144632 A1 | 11/2008 |
| WO | 2011/096006 A1 | 8/2011 |

(Continued)

OTHER PUBLICATIONS

Extended search report of the European Patent Office dated Oct. 21, 2015 in European patent application 14002094.2-1652 on which the claim of priority is based.

(Continued)

*Primary Examiner* — Alyssa M Alter
(74) *Attorney, Agent, or Firm* — Walter Ottesen, P.A.

(57) ABSTRACT

A laser treatment head guides a laser beam to a target area within a body cavity and includes a laser output element having a deflection element. The laser output element with deflection element is rotatable relative to a guide element about an axis. First and second thread elements mutually engage to cause the deflection element to perform a combined axial and rotational movement relative to the guide element. A control unit and the laser treatment head are configured such that the target area is irradiated by individual pulses (p) in a helical pattern of irradiation spots over a section of the circumference of the body cavity. The control unit is further configured such that reference locations (X) on the target area are irradiated by an individual pulse number (N) of subsequent pulses (p), thereby heating the mucosa tissue within the target area to a predetermined temperature.

42 Claims, 5 Drawing Sheets

(51) Int. Cl.
*A61B 17/00* (2006.01)
*A61B 18/00* (2006.01)
*A61N 5/067* (2006.01)

(52) U.S. Cl.
CPC ............ *A61B 2017/00172* (2013.01); *A61B 2018/005* (2013.01); *A61B 2018/00196* (2013.01); *A61B 2018/00208* (2013.01); *A61B 2018/00327* (2013.01); *A61B 2018/00517* (2013.01); *A61B 2018/00523* (2013.01); *A61B 2018/00559* (2013.01); *A61N 2005/061* (2013.01); *A61N 2005/0605* (2013.01); *A61N 2005/0606* (2013.01); *A61N 2005/067* (2013.01); *A61N 2005/0608* (2013.01); *A61N 2005/0611* (2013.01); *A61N 2005/0626* (2013.01); *A61N 2005/0665* (2013.01); *A61N 2005/0666* (2013.01)

(58) Field of Classification Search
USPC .......................................................... 607/89
See application file for complete search history.

(56) References Cited

FOREIGN PATENT DOCUMENTS

| | | |
|---|---|---|
| WO | 2012/037954 A1 | 3/2012 |
| WO | 2015/014811 A1 | 2/2015 |

OTHER PUBLICATIONS

Extended search report of the European Patent Office dated Dec. 8, 2014 in European patent application 14002094.2-1652 on which the claim of priority is based.

\* cited by examiner

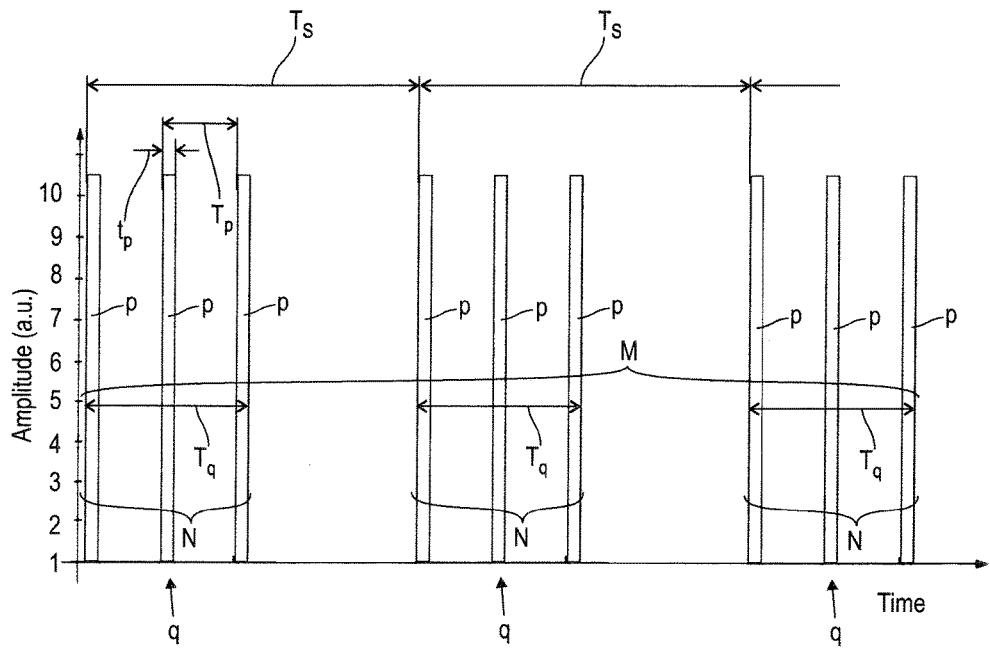
Fig. 5
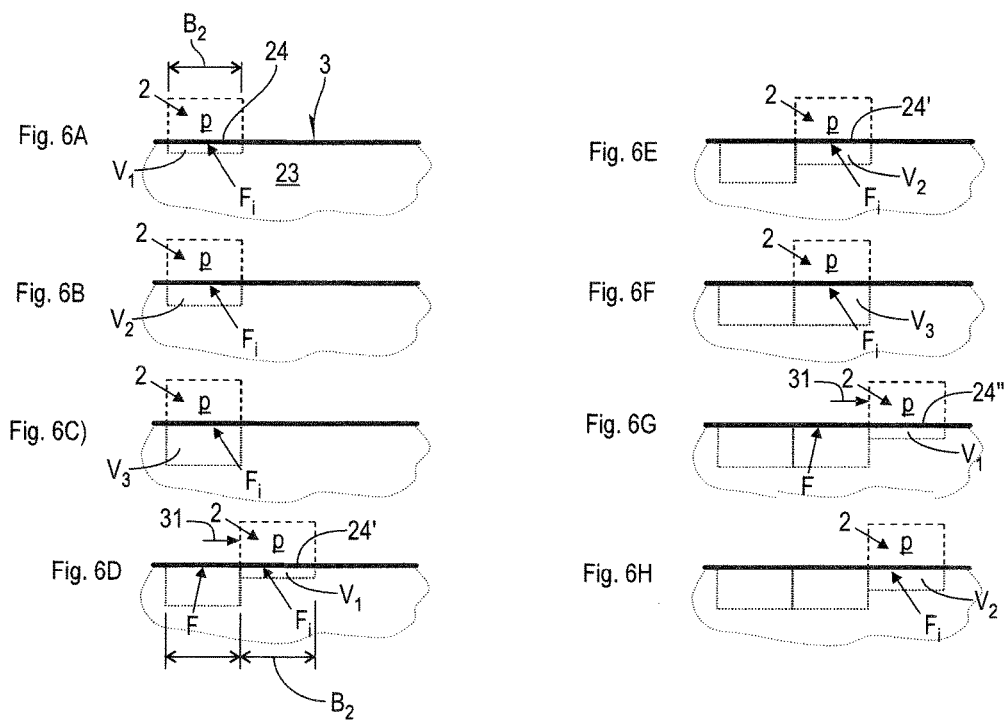

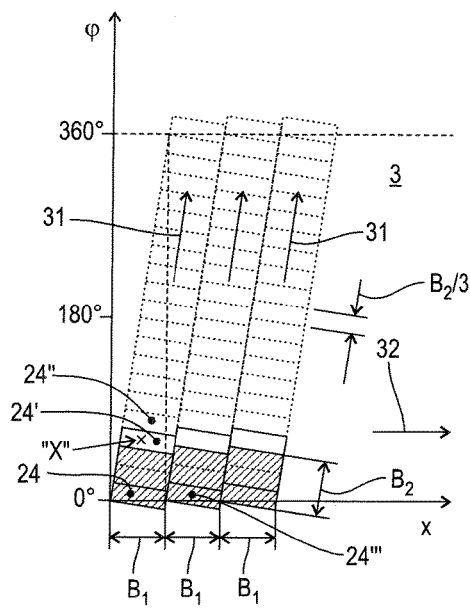
Fig. 7
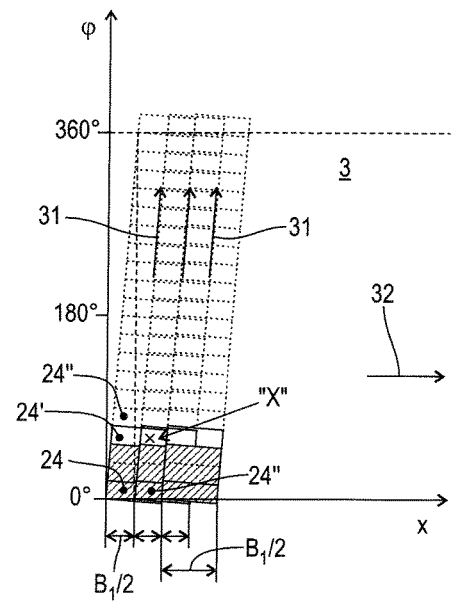
Fig. 8
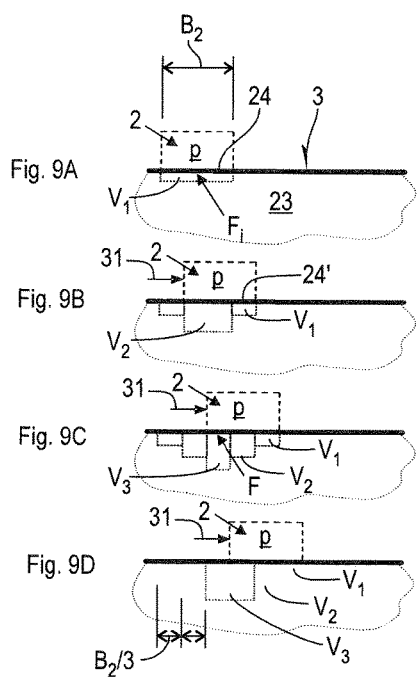
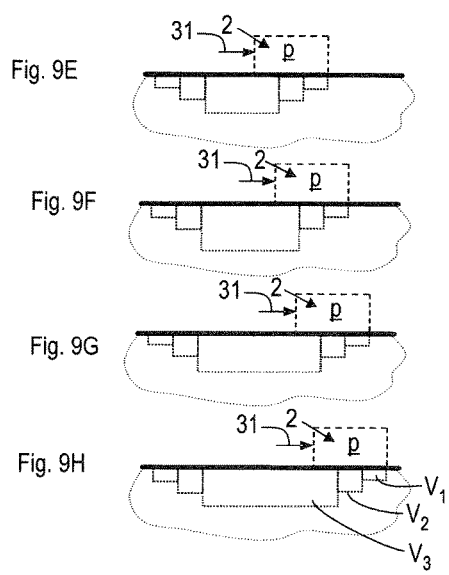

LASER SYSTEM AND LASER TREATMENT HEAD THEREFOR

CROSS REFERENCE TO RELATED APPLICATION

This application claims priority of European patent application no. 14002094.2-1652, filed Jun. 18, 2014, the entire content of which is incorporated herein by reference.

FIELD OF THE INVENTION

The present invention relates to a laser treatment head and a laser system for thermal, non ablative, or minimally ablative treatment of tissues which line body cavities, and are exposed to the external environment. Examples of the body cavities include the vagina, the mouth, the ears, the penis, the urethra, and the anus.

BACKGROUND OF THE INVENTION

In what follows, the treatment of mucous tissue and female genital problems are described in more detail but the invention applies also to the treatments of other tissues and body cavities.

Mucosa is the moist tissue that in addition to some human organs lines body cavities. There are a number of health problems that are caused by a deteriorating laxity, elasticity and tightness of mucous membranes and the underlying adjacent tissues (muscles et cetera) The following are some of the most common problems: a) involuntary loss of urine called urinary incontinence (UI) among women; b) loss of anal sphincter control leading to the unwanted or untimely release of feces or gas called anal or fecal incontinence; c) vaginal relaxation and the loss of sexual gratification in women and d) snoring.

Mucous tissue is rich with collagen, a protein which is responsible for the vaginal tissue's elasticity and turgor. Collagen is also the most important component of the muscular tissue's endomysium. The metabolism of collagen degrades with age which leads to deteriorating laxity, elasticity and tightness of mucous membranes and the underlying adjacent tissues (muscles et cetera) The loss of the optimal structure of uterus is not only a consequence of aging, but is also a consequence of injuries during child delivery. Multiple vaginal deliveries and in particular deliveries with the assistance of instruments are additional risk factors for injuries to vagina and pelvic floor. The most common consequence of the above chain of events is urinary incontinence. Clinical studies show that about 30% of women in the reproductive period experience problems with involuntary leakage of urine. However, only approximately 25% of these women decide to seek professional help. Due to the involuntary urine leakage approximately the same percentage of women is also not satisfied with their sexual life. In addition, the vaginal relaxation diminishes the sense of contact during the intercourse, which in turn influences the sexual gratification and quality of life. Other problems related to the degradation of female genital mucous tissues include but are not limited to the vaginal prolapse (pelvic organ prolapse) and atrophic vaginitis (vaginal dryness).

Several approaches have been developed to address the issue of deteriorating body cavity tissues. The most common current technique utilizes a surgical procedure that requires the cutting and rearrangement of the tissue in order to reformat the body cavity. Operating on or near sensitive tissues is inherently risky and can cause scarring, nerve damage and decreased sensation. Furthermore, patients require an extended recovery period.

It is well known that heat pulsing (that is, temporarily increasing the temperature) of collagen can not only improve the collagen structure but also initiate neo-collagenesis, that is, the generation of new collagen. As a result of the temperature increase, the intermolecular cross-links are broken which stabilizes the collagen's triple-helix structure, and leads to the collagen shrinkage. This suggests that heat pulsing of the endopelvic fascia and pelvic floor tissue could represent an effective, non-surgical method for treating female urinary incontinence and vaginal relaxation syndrome. Radio-frequency (RF) devices have been cleared for treating female stress urinary incontinence, elevating temperatures of submucosa around the bladder neck and proximal urethra to about 65° C. However, the treatments with RF devices are deep and invasive, presenting higher risks of adverse effects such as: dysuria, urinary retention, post-op pain and urinary tract infections. Also, since the RF energy is delivered transurethrally, these treatments are painful, and require anaesthesia.

Many experimental and clinical studies up to date have demonstrated the benefits of laser technology for treating conditions and illnesses resulting from damaged collagen. Most of the progress has been made in the area of dermatology and aesthetic medicine. However, from U.S. Pat. No. 8,709,057 an apparatus and method are known, using a laser for treating mucous tissue in body cavities which is based on a non-ablative heat pulsing of the body cavity wall with a laser. According to the above prior art apparatus and method, the laser system comprises a laser source for generating a laser beam, a control unit and a hand piece for manually guiding the laser beam onto a body cavity, such as the vagina wall.

However, there are some significant limitations when applying prior apparatus to treat the interior body cavity wall. The prior art procedure is slow and requires constant attention of the operator. For example, a typical vaginal procedure according to the prior art consists of the following steps: i) a speculum is inserted into the patient's vagina; ii) a laser handpiece adapter with either a flat or angular mirror is inserted into the speculum; iii) with the handpiece adapter fully inserted and the mirror properly oriented, the practitioner starts delivering laser energy per each location; iv) after an appropriate amount of laser energy has been delivered to a certain location, the laser handpiece adapter is manually rotated and/or moved longitudinally within the speculum in order to be able to irradiate a different location on the vaginal wall; v) this procedure is repeated until substantially the whole interior vaginal wall has been irradiated.

SUMMARY OF THE INVENTION

It is an object of the invention to provide an improved laser treatment head, having a simple, reliable configuration, and allowing for a quick, efficient laser delivery with reproducible irradiation distribution.

This object is solved by a laser treatment head for guiding a laser beam to a target area within a body cavity, the laser treatment head including: a laser output element defining and extending along a longitudinal axis; the laser output element including a carrier member and being configured to output a laser beam; a guide element for the laser output element configured to have an incoming, substantially coaxial laser beam section of the laser beam pass therethrough during operation; the laser output element further including a deflection element configured to deflect the incoming, substantially coaxial laser beam section into a substantially radial output laser beam section; the deflection element being fixed to the carrier member; the laser output element including the deflection element being configured to be rotatable relative to the guide element about the longitudinal axis; the carrier member including a first thread element; the guide element including a second thread element; and, the first thread element and the second thread element being configured to mutually engage so as to cause the deflection element to perform a combined axial and rotational movement relative to the guide element in response to a rotational movement of the laser output element relative to the guide element.

It is a further object of the invention to provide an improved laser system with improved speed and accuracy, and with minimized impact on the patient's organism.

This object is solved by a laser system for thermal treatment of mucosa tissue within a target area in a body cavity, the laser system including: a laser source configured to generate a laser beam; a laser treatment head for guiding the laser beam to a target area within a body cavity; the laser treatment head including a laser output element and a guide element; the laser output element defining and extending along a longitudinal axis; the laser output element including a carrier member; the guide element for the laser output element configured to have an incoming, substantially coaxial laser beam section of the laser beam pass therethrough during operation; the laser output element further including a deflection element configured to deflect the incoming, substantially coaxial laser beam section into a substantially radial output laser beam section; the deflection element being fixed to the carrier member; the laser output element including the deflection element being configured to be rotatable relative to the guide element about the longitudinal axis; the carrier member including a first thread element; the guide element including a second thread element; the first thread element and the second thread element being configured to mutually engage so as to cause the deflection element to perform a combined axial and rotational movement relative to the guide element in response to a rotational movement of the laser output element relative to the guide element; a motor; a control unit configured to control the drive speed of the motor and to control the laser source so as to generate the laser beam in individual pulses (p); the control unit and the laser treatment head being configured such that the target area is irradiated by the individual pulses (p) in a helical pattern of irradiation spots over at least a section of the circumference of the body cavity; and, the control unit is further configured such that reference locations (X) on the target area are irradiated by an individual pulse number (N) of subsequent pulses (p) thereby heating the mucosa tissue within the target area to a predetermined temperature.

In order to understand our invention, one must realize that there are generally three steps in soft tissue heating when exposing tissue to pulsed laser radiation. The tissue is first heated directly (first step) within the optical absorption depth $d_{opt}$. Direct heating occurs during the course of the laser pulse only. Since water is the major constituent of soft tissues, the optical absorption depth depends on how strongly a particular laser wavelength is absorbed in water. For example, for "water transmitted" laser wavelengths the optical absorption depth is relatively large, and may be approximately 15 mm (diode laser with wavelength $\lambda=0.8$ μm), 5 mm (Nd:YAG laser; $\lambda=1.064$ μm), or 1 mm (Nd:YAP laser; $\lambda=1.340$ μm). For the so-called "water absorbed" laser wavelengths the absorption depth is small, and may be approximately 400 μm (Ho:YAG laser; $\lambda=2.1$ μm), 30-100 μm ($CO_2$ laser; $\lambda=9$-10 μm), 10 μm (Er:YSSG or Er, Cr:YSGG laser; $\lambda=2.7$-2.8 μm), or 3 μm (Er:YAG laser; $\lambda=2.9$ μm).

Direct heating is followed by thermal diffusion (second step) that indirectly heats the deeper lying tissues. This occurs during the laser pulse, continues for a while after the laser pulse, and is accompanied by indirectly heating deeper lying tissue up to $x_p$.

The depth to which heat diffusion transports laser generated heat deeper into the tissue can be estimated by calculating the characteristic thermal diffusion depth $x=(4D\,t)^{1/2}$, t being the temporal duration of diffusion and D being the diffusion constant for soft tissue which is about $1\times10^{-7}$ $m_2$/s. For shorter pulses, the time span for thermal diffusion is short, and the heat energy does not reach very deep into the tissue. For longer pulses, the heat has sufficient time to spread deeper into the tissue.

The third step occurs only when the laser pulse fluence is sufficiently high to heat the thin surface layer up to the water evaporation temperature above 100° C. This would lead to the ablation of the superficial tissue layers; but it is the goal of the inventive laser system and method to avoid or minimize this ablation, that is to avoid or minimize the third step.

The inventive laser system and method are based on the concept of controlled heat deposition or introduction into the soft tissue and this requires an effective and safe heat source that is capable of distributing heat approximately 50 to 500 microns deep into mucosa, thereby neither damaging the outside mucous tissue surface nor the deeper lying surrounding tissues. One could consider to achieve this goal by utilizing a direct heating scheme where a laser source with the optical penetration depth approximately matching the desired depth of heat penetration is used. However, with this direct heating approach, the depth of heat deposition is not adjustable. In addition, the available laser penetration depth may be too large or too small, and may thus not be optimal for achieving the desired effect in a safe and effective manner.

Alternatively, and according to the invention a laser wavelength with a short penetration depth may be used, and the desired larger depth of heat penetration is achieved indirectly by using the inventive heat pulsing scheme. By utilizing the heat pulsing scheme, heat which is generated by the laser light on the tissue's surface is transported deeper into the bulk tissue by means of heat diffusion, thus preventing the surface temperature from getting dangerously elevated. Especially lasers with "water absorbed" wavelengths, that is, holmium (λ around 2 μm) erbium (λ around 3 μm) and $CO_2$ (λ around 9-10 μm) lasers, are useful. The most important requirement is that the laser light is absorbed within a very thin superficial tissue layer, effectively making it a non-contact "hot iron" heat source.

The thickness of mucosa varies but typically mucosa has a thickness of several hundred microns. For controlled heating of mucosa tissue, an effective and safe method is needed for heating the bulk of the mucous tissue layer to a depth of at least 100 microns, preferably of approximately 300-500 microns without damaging any deeper-lying surrounding tissues and organs. The depth of non-ablative heat introduction can be increased by repetitive stacking of sub-ablative laser pulses. Pulse stacking can result in a ten-fold increase in the depth of thermally affected soft tissue. This is due to the fact that diffusion continues also during the off periods between the pulses, increasing the depth of thermally affected layer to $x_d$.

The objective for increasing the depth of thermal effects is to achieve controlled heat-induced denaturing (that is, damage) of the bulk tissue collagen that leads to subsequent synthesis of new collagen with as little as possible damage to the surface tissue.

The heat pulsing method used for treating mucous tissue, and female urinary incontinence in particular, is based on the above concept of pulse stacking of non-ablative low-fluence laser pulses, which is referred to as "heat pumping" of mucous tissue. The concept of pulse stacking (consecutive pulse train) is as follows.

According to the prior art apparatus and method (U.S. Pat. No. 8,709,057), the laser sources must be pulsed, with pulse widths from 1 microsecond to 10 seconds. The lower temporal limit ensures that the instantaneous pulse power remains in the linear thermal range of the laser-tissue interactions. Namely, at high laser powers, the laser tissue interaction can become non-linear leading to ionization and optical breakdown, which may result in an undesirable damage to the tissue. And the upper pulse duration limit ensures that the generated heat does not spread via diffusion too far away from the irradiated surface. Namely, the direct heating by the laser light is followed by thermal diffusion that indirectly heats the deeper lying tissues (indirect heating). For shorter pulses, the time span for thermal diffusion is short, and the heat energy does not reach very deep into the tissue. For longer pulses, the heat has sufficient time to spread deeper into the tissue. The distance to which the heat will diffuse during a laser pulse of a certain pulse width, the pulse duration $t_p$, can be estimated from $x_d = (4D \, t_p)^{1/2}$. The upper pulse duration limit of 10 sec thus limits the diffusion depth $x_d$ to below 2 mm, that is, below the thickness where any sensitive underlying tissues and organs are located. The pulse duration of the single pulses is preferably in a range from 10.0 µs, inclusive, to 2.000 µs, inclusive, and is in particular at least approximately 600 µs, which showed in practice best results.

Further, since a non-ablative (or only minimally ablative), and predominantly thermal treatment of the tissue is desired the fluence of each laser pulse must be below or close to the ablation threshold fluence. The fluence is defined as energy density: F=E/S where E is the energy of the laser pulse, and S is the surface area of the laser irradiation spot. Usually it is calculated in $J/cm^2$. The ablation threshold depends on the laser wavelength, and is lower for more strongly absorbed laser wavelengths. The ablation threshold depends also on the pulse duration, and is lower at longer pulse durations. Appropriate laser parameters will depend on the type of the laser system used and on the specific treatment indication. For example, for water absorbed wavelengths the threshold will be higher in moist cavities such as vagina and mouth where mucous tissue is typically covered by a layer of water containing bodily fluids.

According to the prior art apparatus and method, a "stamping" technique is being used whereas the laser beam with a certain spot size is fixated to the same area until the required sequence of N pulses has been stacked upon each other, and then the beam is consecutively moved from spot to spot until the whole area has been treated. Every single pulse sequence consisting of N individual pulses forms a single "smooth pulse", which follow each other in the sequence "smooth pulse" repetition time $T_p$, thereby introducing high amounts of energy E into the mucosa tissue without ablation or damage of the mucosa tissue for a non-ablative, pure thermal, or alternatively minimally ablative treatment.

It may be more energy efficient for a particular laser configuration to operate with relatively short pulse repetition times. In such a case the duration of the irradiation of the target area on the tissue during which the required cumulative fluence is delivered may be according to the prior art apparatus and method prolonged by delivering laser energy in multiple, M "smooth pulse" sequences which follow each other in the multiple pulse repetition time $T_s$. In this case, the spot size is fixated to the same area until all K=M×N pulses have been stacked upon each other. The laser beam is then moved to a next spot and the multiple smooth pulse irradiation sequence is initiated again. It should be appreciated that a single "smooth pulse" energy delivery as described in the preceding paragraph corresponds to a special case with M=1, leading to a total of K=N pulses received on one irradiation spot.

When the temporal separation among the pulses is longer than the thermal relaxation time (TRT) of the mucous surface tissue (estimated to be in the range of 10-100 msec), the surface mucous tissue has sufficient time to cool between the pulses by dissipating the heat into the deeper tissue layers. Thus temperatures required for ablation are reached at much higher fluences. The TRT is the time required for the tissue temperature to decrease by approximately 63%. And if at the same time the laser energy is delivered in a time period that is shorter than the TRT of the total bulk mucous layer (estimated to be in the range of 0.5-10 sec) then the deeper lying mucous layer does not have time to cool off during the laser pulse sequence. Laser energy is transmitted as heat onto the mucosa without causing any ablation, or only minimal ablation, and then dissipates into the deeper tissue layers. The delivered laser energy thus results in an overall non-ablative, or minimally ablative build-up of heat and creates a temperature increase deep in the mucous and sub-mucous tissue.

We have determined that with this heat pumping method the mucous tissue can be heated to temperatures in the range from 40 to 70 degrees Celsius, preferably in the range from 42 to 65 degrees Celsius, and this temperature range has been identified as being required to achieve reversible tissue damage leading to tissue shrinkage and new collagen generation.

A disadvantage of the prior art pulse "stamping" method is that it requires a relatively complex control of the movement of the laser beam, especially when it is performed manually. The optical delivery system must be positioned to deliver a beam to a certain spot and left there unmoved until the whole sequence of K pulses has been delivered (stacked) to the same area, and then the optical delivery system must be moved to another area and kept there fixed until another sequence of pulses has been delivered.

Based on these findings an inventive laser treatment head is proposed, having a laser output element with deflection means and a guide element. The laser output element including its deflection means is rotatable relative to the guide element about the longitudinal axis. The carrier member comprises first thread means, wherein the guide element comprises second thread means, and wherein the first and second thread means engage each other such that, upon rotational movement of the laser output element relative to the guide element, the deflection means perform a combined axial and rotational movement relative to the guide element.

The related inventive laser system comprises the laser treatment head, a laser source for generating a laser beam, and a control unit for controlling the motor drive speed of the laser treatment head and for controlling the operation of the laser source to generate the laser beam in individual pulses. The control unit and the laser treatment head are configured such that the target area is irradiated by individual pulses in a helical pattern of irradiation spots over at least a section of the circumference of the body cavity. The control unit is further configured such that respective reference locations on the target area are irradiated by an individual pulse number of subsequent pulses, thereby heating the mucosa tissue within the target area to a predetermined temperature.

Thereby, the inventive laser system is adapted to perform the related inventive method, according to which a treatment portion of the laser treatment head is inserted into the body cavity. The laser output element of the laser treatment head is rotationally driven relative to the guide element while keeping the guide element in a fixed position relative to the body cavity, thereby moving the laser output element in a combined rotational and axial movement. The laser beam is generated in individual pulses by means of the laser source under control of the control unit. The laser beam is guided to the target area by means of the laser treatment head, wherein the target area is irradiated by individual pulses in a helical pattern of irradiation spots over at least a section of the circumference of the body cavity. Respective reference locations on the target area are irradiated by a heat pumping number of subsequent pulses, thereby heating the mucosa tissue within the target area to a predetermined temperature.

The treatment head and laser system according to the invention provide simple and reliable means for achieving an exactly reproducible irradiation pattern such that direct and subsequent indirect heating of the mucosa tissue is achieved in an evenly spread manner, to the desired depth and temperature, and by avoiding or minimizing ablation related to the heating of the thin surface layer up to the water evaporation temperature above 100° C. Even more detail features of the invention and related advantages become apparent from the drawings and the related description.

BRIEF DESCRIPTION OF THE DRAWINGS

The invention will now be described with reference to the drawings wherein:

FIG. 5 illustrates an exemplary pulse sequence of the laser beam generated by the laser system according to FIG. 1, and delivered to the target area by the laser treatment head according to FIGS. 2 to 4;

FIGS. 6A to 6H illustrate in a schematic view the tissue heat diffusion when irradiated in a "stamped" manner with the irradiation pattern according to FIG. 5;

FIG. 7 illustrates a schematic developed view an "overlapping" irradiation pattern achieved by the laser treatment head according to FIGS. 2 to 4 in connection with the pulse sequence according to FIG. 5, with irradiation spots overlapping each other in the helical relocation direction;

FIG. 8 illustrates a schematic developed view an alternative "overlapping" irradiation pattern achieved by the laser treatment head according to FIGS. 2 to 4 in connection with the pulse sequence according to FIG. 5, with irradiation spots overlapping each other both in the helical relocation direction and in the axial direction;

FIGS. 9A to 9H illustrate in a schematic view the tissue heat diffusion when irradiated in an "overlapping" manner with the irradiation pattern according to FIGS. 5, 7 and 8;

DESCRIPTION OF THE PREFERRED EMBODIMENTS OF THE INVENTION

Figure 1:
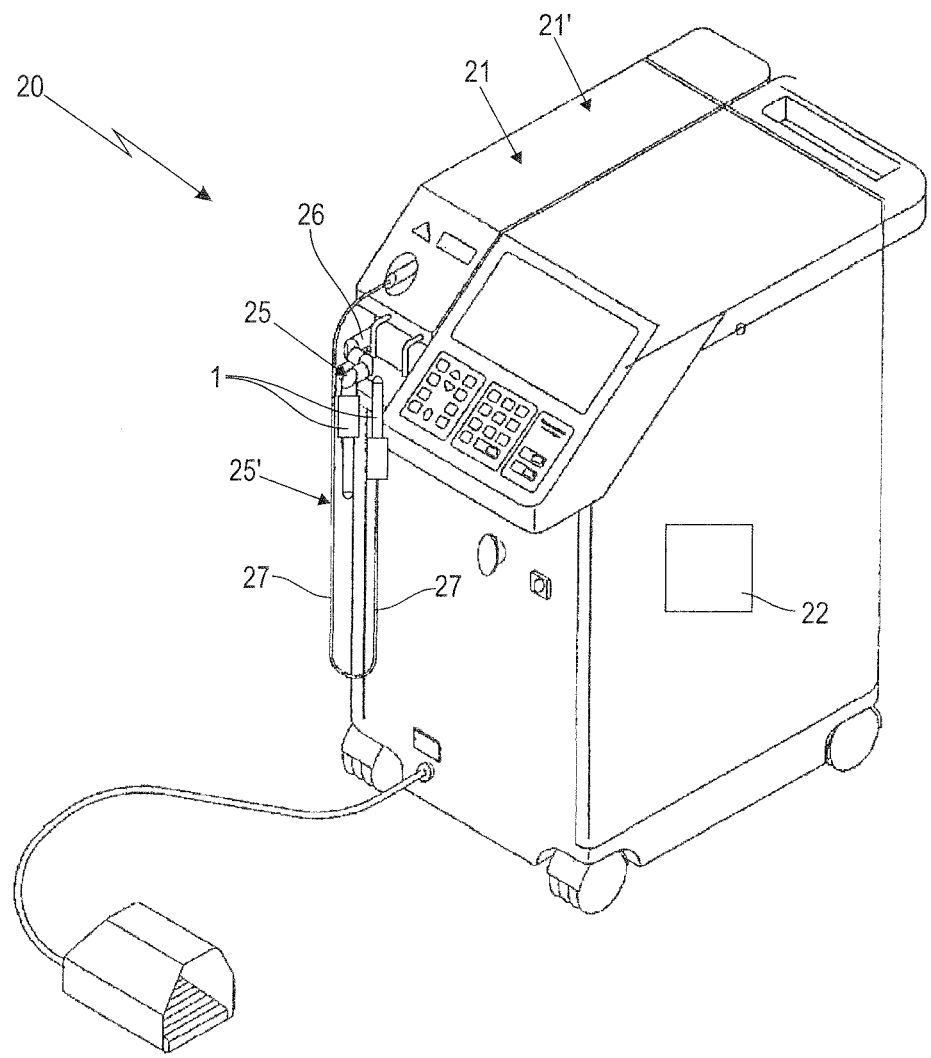
FIG. 1 illustrates an inventive laser system with both an optical fiber laser delivery system and an articulated arm laser delivery system.

With reference now to FIG. 1, a medical treatment laser system 20 according to the invention comprises at least one laser source (21, 21') for generating a laser beam (2, 2') (FIGS. 2 to 5), and at least one optical delivery system (25, 25') for the laser beam (2, 2'). The laser system further comprises a schematically indicated control unit 22 for controlling the operation of both the laser source (21, 21'), including the generated laser beam (2, 2') parameters, and the operation of a laser treatment head 1 as described below in connection with FIGS. 2 to 5.

In one preferred embodiment the optical delivery system 25 includes an articulated arm 26 and a manually guided laser treatment head 1 (FIGS. 2 to 5) connected to the distal end of the articulated arm 26, wherein the laser beam (2, 2') is transmitted, relayed, delivered, and/or guided from either or both laser sources (21, 21') through the articulated arm 26 and the laser treatment head 1 to a target. The articulated arm 26 might preferably be an Optoflex® brand articulated arm available from Fotona, d.d. (Slovenia, EU). In the shown preferred embodiment, a second optical delivery system 25' for use with the laser treatment head 1 (FIGS. 2 to 5) is provided, wherein instead of the articulated arm 26, a flexible elongated delivery fiber 27 for guiding the laser beam (2, 2') from either or both laser sources (21, 21') is incorporated. Despite both laser sources (21, 21') and delivery systems (25, 25') being shown in combination, one of both in the alternative may be provided and used within the scope of the present invention.

In another preferred embodiment, the laser sources 21 and 21' are controlled and operated in such a manner that at least one of the laser beams (2, 2') from the laser sources (21, 21') is delivered to the treatment head 1 through a first optical delivery systems 25, or a second optical delivery system 25' simultaneously with the second laser beam (2, 2') being delivered through a first optical delivery system 25, or a second optical delivery system 25'.

In yet another embodiment, the laser sources 21 and 21' may be controlled and operated in such a manner that laser beams (2, 2') are delivered to the treatment head 1 in a sequential manner. The sequential manner may be such that the irradiation from laser beams (2, 2') alternate one after the other, however any other temporal pattern of sequentially delivered beams may be applied.

Alternatively, one or both laser sources (21, 21') may be built into the laser treatment head 1 whereas the laser treatment head 1 itself represents one or both optical delivery systems (25, 25') for the laser beam (2, 2'). Moreover, the control unit 22, or a complete medical laser system 20 may be built into the laser treatment head 1 as well.

Figure 2:
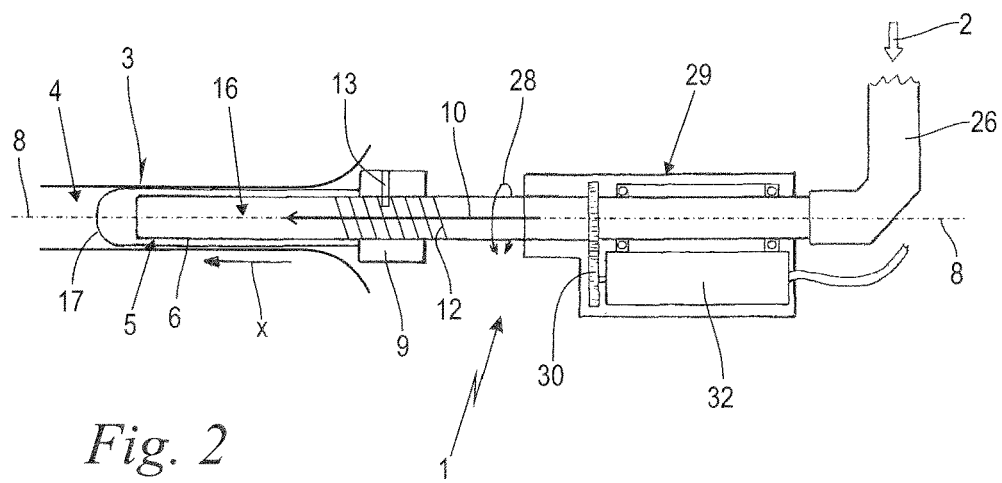
FIG. 2 illustrates in a schematic section view an exemplary laser treatment head fed by an articulated arm, having a motorized output element.

FIG. 2 shows in a schematic sectional view a laser treatment head 1 for use as part of the laser system 20 according to FIG. 1. The laser treatment head 1 is connected to the distal end of the articulated arm 26. However, the laser treatment head 1 may, in the alternative, be connected to the distal end of the elongated fiber 27 as shown in FIG. 1.

The laser treatment head 1 comprises a laser output element 5 which extends along a longitudinal axis 8, and which is rotatable about the longitudinal axis 8 according to arrow 28. The laser treatment head 1 further comprises a guide element 9 for the laser output element 5, which is positioned by the user in place, where desired. An optional part of the guide element 9 is a speculum 17 made of a material transparent to the laser beam 2, wherein the speculum 17 is fixedly connected to the guide element 9 base body, and held in a place together with the guide element 9. The speculum 17 may be replaced by a wire mesh or other suitable radial distance means wherein the speculum 17, the wire mesh or other suitable radial distance means are adapted to insert a treatment portion 16 of the treatment head 1 into a body cavity 4, while allowing free rotational and axial movement of the output element 5 within the body cavity 4. The above-mentioned treatment portion 16 is the portion of the laser treatment head 1 extending from the guide element 9 to the distal end of the output element 5, and being inserted into the body cavity 4.

In the shown embodiment, the output element 5 comprises an elongate carrier member 6 in form of a hollow tube. The laser beam (2, 2') is generated by either one or both of the laser sources (21, 21') of the laser system 20 according to FIG. 1, and is fed into the treatment head 1 by means of the articulated arm 26 or the elongated fiber 27 such that during operation an incoming laser beam section 10 of the laser beam (2, 2') passes in general coaxially to the longitudinal axis 8 through the hollow carrier member 6. Instead of the shown tube shape, the carrier member 6 may have any other shape or configuration which allows the incoming laser beam section 10 to pass as shown and as described above.

Figure 3:
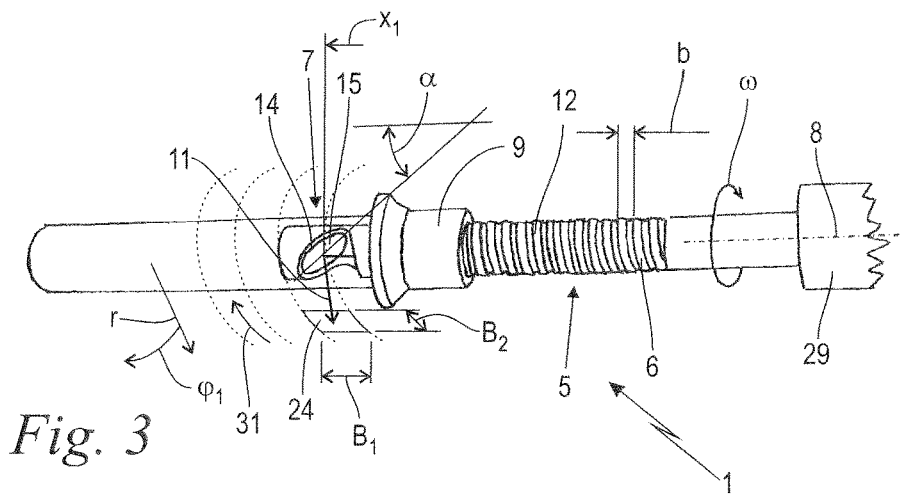
FIG. 3 illustrates the laser treatment head according to FIG. 2 with retracted output element.
Figure 4:
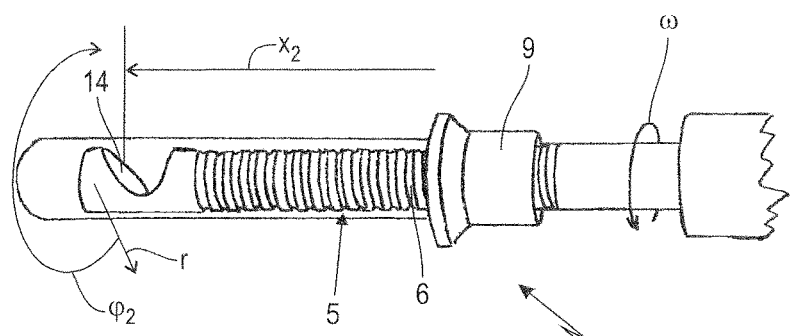
FIG. 4 illustrates the laser treatment head according to FIG. 2 with extended output element.

As shown in FIGS. 3 and 4, and as described infra in more detail, the output element 5 further comprises—in addition to the carrier member 6—deflection means 7 for deflecting the incoming laser beam section 10 into an output laser beam section 11 such that the output laser beam section 11 exits the output element 5 in a direction being generally radial to the longitudinal axis 8.

As schematically shown in FIG. 2, the carrier member 6 has on its outer circumferential surface first thread means 12, wherein the guide element 9, which surrounds the carrier member 6 in the area of the first thread means 12, has on its inner side facing the first thread means 12, relating second thread means 13, which engage into the first thread means 12. The first thread means 12 are embodied as a helical groove, while the second thread means 13 are embodied as a radially protruding pin, which engages the helical groove of the first thread means 12. However, first and second thread means (12, 13) may in the alternative be embodied as a regular nut and bolt thread. In any case first and second thread means (12, 13) engage each other such that upon rotational movement of the laser output element 5 relative to the guide element 9, as indicated by an arrow 28, the entire output element 5 including the carrier member 6 and the deflection means 7 (FIGS. 3, 4) perform a combined axial and rotational movement relative to the guide element 5, wherein the axial movement is performed in an axial direction (x). Thereby, the guide element 9 functions as a bearing for the output element 5 to allow both the rotational and axial relative movements.

The rotational movement of the output element 5 may be performed manually by the user. However, according to a preferred embodiment of the invention, a drive unit 29 with a motor 32 is provided, having bearings to allow for a rotational movement of the output element 5 relative to the drive unit 29. The motor 32, which is in the preferred embodiment an electric motor, drives the output element 5 by means of a schematically indicated gear 30 such that the output element 5 performs a rotational movement according to arrow 28, while keeping an axially fixed relative position to the drive unit 29. In consequence, and upon the above described combined rotational and axial movement of the output element 5 relative to the guide element 9, the drive unit 29 follows the axial movement without performing any own rotational movement. However, the configuration of the drive unit 29 may be changed within the scope of the invention such that the drive unit 29 is fixedly connected to the guide element 9, wherein the rotating output element 5 performs the combined rotational and axial movement relative to both the guide element 9 and the drive unit 29. In any case, only one single motor 32 is provided and required to generate the combined rotational and axial movement.

The shown inventive laser treatment head 1 and, respectively, the entire laser system 20 according to FIG. 1 is adapted and configured for thermal treatment of mucosa tissue 23 (FIGS. 6A to 6H and 9A to 9H) within a target area 3 in a body cavity 4 as schematically depicted in FIG. 2. The thermal treatment is a non-ablative and/or minimally ablative treatment of the mucosa tissue 23 which lines the body cavity 4. Examples of the body cavities 4 include the vagina, the mouth, the ears, the penis, the urethra, and the anus. As can be seen in FIG. 2, the user inserts the distal end of the laser treatment head 1, that is the treatment portion 16 into the body cavity 4 and keeps the guide element 9 manually in the desired position. In the alternative, positioning of the guide element 9 may be performed mechanically by suitable means. The speculum 17 or the above-mentioned alternative means keep the body tissue of the circumferential body cavity 4 wall in a defined radial distance to the output element 5, thereby allowing to focus the output beam section 11 (FIGS. 3, 4) exactly on the desired target area 3 as part of the body cavity 4 inner wall. While keeping during operation the guide element 9 in a pre-determined position relative to the body cavity 4, the output element 5 does not only perform a combined rotational and axial movement relative to the guide element 9, but also the same combined rotational and axial movement relative to the target area 3 on the body tissue of the body cavity 4 inner circumferential wall.

Figure 10:
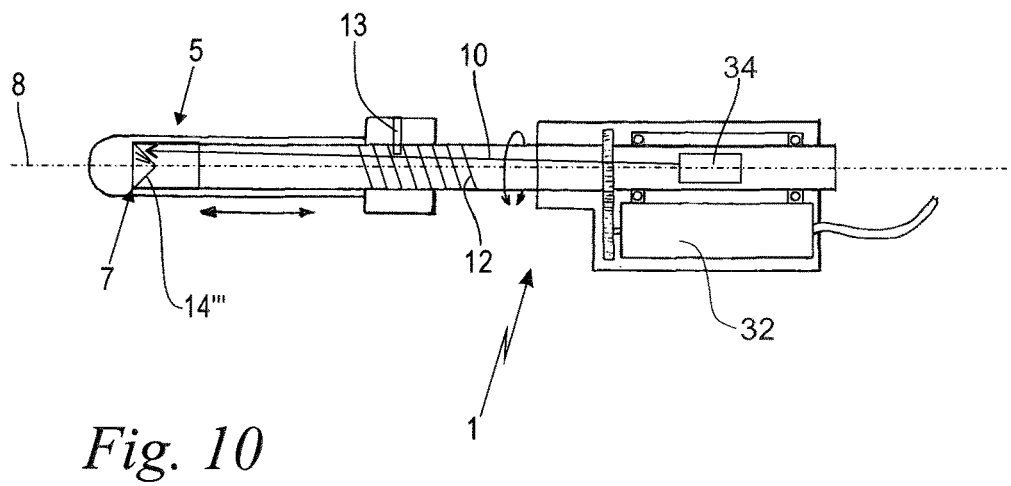
FIG. 10 illustrates in a schematic view a variant of the laser treatment head according to FIG. 2 having a scanner and a conical shaped mirror.

FIG. 3 shows in a perspective and schematic view the laser treatment head according to FIG. 2, wherein the output element 5 is shown in a retracted position relative to the guide element 9. It can be further seen, that deflection means 7 are provided and fixed to the carrier member 6 such that the deflection means 7 perform the same combined rotational and axial movement as the carrier member 6. In the shown preferred embodiment the deflection means 7 are a mirror, here a flat mirror 14 having a flat reflecting surface 15. The mirror 14 is fixed to the carrier member 6 such that an angle α between the reflection surface 15 and the longitudinal axis 8 of the laser output element 5 is in a range from 30° to 60°. In the shown preferred embodiment, the angle α is approximately 45°. The angle α is chosen to reflect the incoming laser beam section 10 (FIG. 2) into the above-mentioned generally radial output laser beam section 11. As an alternative an optical element using refraction and/or internal reflection may be used. In any case optical means (not shown) are provided and embodied such that, during one single laser pulse (p) (FIG. 5), the laser beam (2, 2') irradiates a defined irradiation spot 24 of defined shape and size on the target area 3 (FIG. 2). The deflection means 7 may be part of the aforementioned optical system which includes the option that the mirror 14 and its reflection surface 15 deviate from the flat shape. In one of the preferred embodiments, the deflection means 7 may consist of a conical mirror 14''' as shown in FIG. 10, however, within the present context, without a scanner 34 of FIG. 10. Because of the conical shape of the mirror the incoming laser beam section 10 is spread in all radial directions thereby producing a cylindrical irradiation pattern around the longitudinal axis 8. In another one of the preferred embodiments, the deflection means may, instead of a conical mirror, consist of multiple flat mirrors 14" of triangular shape (FIG. 11), being arranged to form a pyramid. In yet another one of the preferred embodiments, the deflection means 7 is a pair of opposite inclined flat mirrors 14' with non-reflecting front faces 33 in between (FIG. 12). Again, in both aforementioned embodiments, the scanner 34 may be omitted, while the flat mirrors 14' or the multiple flat mirrors 14" are just a replacement for the single flat mirror 14 in the embodiment of FIGS. 1 to 4.

Although it is desired to generate the defined shape and size of the irradiation spot 24 on the target area 3 of the body cavity 4, one has to take into account the above mentioned function of the speculum 17, which holds the target area 3 on its outer surface. With respect to their location relative to the treatment portion 16 the target area 3 and the outer surface of the speculum 17 are identical. One can therefore define shape, size focal area and motion path of the irradiation spots 24 on the outer surface of the speculum 17 or the above mentioned other suitable radial distance means therefore.

FIG. 4 shows the laser treatment head 1 according to FIGS. 2 and 3, wherein the output element 5 including its carrier members 6 and its deflections means 7 are located in an extended position relative to the guide element 9. From simultaneously viewing FIGS. 3 and 4 it is evident, that upon driving the output element 5 with a rotational speed ω relative to the guide element 9 in either one of two opposing directions, the output element 5 may be driven back and forth between both shown retracted and extended positions, wherein the deflection means 7 and the output beam section 11 assume different rotation angles ($\varphi_1$, $\varphi_2$) relative to a common radial reference direction (r), and simultaneously different axial insertion positions ($x_1$, $x_2$) in the axial direction (x) (FIG. 2) relative to the guide element 9. It can be further seen from simultaneously viewing FIGS. 3, 4 and 5, that upon doing so the target area 3 is irradiated by subsequent laser pulses (p) (FIG. 5) in a helical pattern of irradiation spots 24 over at least a section of the circumference of the body cavity 4 (FIG. 2). One irradiation spot 24 is followed by subsequent irradiation spots 24 on a helical path. In other words, one individual irradiation spot 24 is relocated relative to the preceding irradiation spot 24 in a helical relocation direction 31, as indicated in FIG. 3, on a helical path as prescribed by the combined rotational and axial movement of the deflection means 7.

In order to better understand the inventive devices and their operational method reference is now simultaneously made to FIG. 1 and FIG. 5. Either one of the laser sources (21, 21') is a laser source generating the laser beam (2, 2') having a wave length λ in a range from above 0.4 μm to 11.0 μm inclusive. Preferably the laser source (21, 21') is a laser with a water absorbing wavelength, such as an Erbium laser generating a laser beam (2, 2') having a wave length λ in a range from above 2.73 μm, inclusive, to 2.94 μm, inclusive. The preferred Erbium laser is in particular an Er:YAG laser generating a laser beam (2, 2') having a wave length λ of 2.94 μm, or an Er, Cr:YSGG or Er:YSGG laser generating a laser beam (2, 2') having a wave length λ in the range from 2.73 μm, inclusive, to 2.79 μm, inclusive. However, any other suitable laser source (21, 21') generating a water absorbed laser beam (2, 2') may be utilized. The control unit 22 of the laser system 20 is adapted to operate the laser source (21, 21') in a pulsed mode, generating the laser beam (2, 2') in single and consecutive pulses (p), as depicted in FIG. 5. According to FIG. 5, the pulses (p) are shown for the sake of simplicity to have a rectangular pulse shape over time. However, in reality the pulse shape is curved having an initial slope until reaching the maximum, and a declining tail. Each laser pulse (p) has a pulse duration $t_p$, which is defined as the time between the onset of the laser pulse (p) and the time when 90% of the total pulse energy has been delivered. According to FIG. 5, the pulses (p) are shown for the sake of simplicity to be of the same duration $t_p$ and amplitude, however the laser source (21, 21') may be operated in a manner that during the irradiation sequence the pulse duration $t_p$ and or amplitude vary from pulse to pulse. For example, in order to further prevent ablation, it may be advantageous for the duration of the pulses (p) to increase from the first to the last pulse in the sequence. And when a minimal ablation is desired, it may be advantageous for the pulse duration $t_p$ to decrease from the first to the last pulse (p) in the sequence. This is due to the fact that the ablation threshold is lower for shorter pulses. Similarly, the amplitude of the pulses may increase or decrease from the first to the last pulse in order to take into account the cumulative increase of the mucous bulk temperature from pulse to pulse. The increase or decrease of the pulse duration and/or of the amplitude may be linear in time, however it may have any other temporal dependence, for example exponential or logarithmic. It may also be advantageous that only the pulse duration and/or the amplitude of the last pulse in the sequence is decreased or increased.

Further reference is made now back to FIG. 3. It can be seen that the optical system of the laser system 20 is adjusted to irradiate irradiation spots 24 on the target area 3 with predetermined size and shape, as mentioned above. For simplicity, the shape of the individual irradiation spots 24 in FIG. 3 is shown to be of a rectangular shape. However, any shapes, including square, polygonal, elliptical or round irradiation spot shapes may be suitable as well. Every individual irradiation spot 24 has, measured in the axial direction (x), a first mean cross section extension $B_1$, and, measured in the helical relocation direction 31, a second mean cross section extension $B_2$. In FIG. 3, the cross extensions ($B_1$, $B_2$) are in first approximation the edge lengths of the rectangle. In case of deviating irradiation spot shapes equivalent mean cross section extensions ($B_1$, $B_2$) have to be derived considering the irradiation mechanism as described infra.

According to FIGS. 1 and 5, the control unit 22 is configured and operated to irradiate a respective location X (FIGS. 7, 8) on the target area 3 by totally K=N×M pulses (p) of the laser beam (2, 2'). Individual pulses (p) are delivered to a respective location in a "smooth pulse"

sequence of N individual pulses (p), each individual pulse (p) having a pulse duration $t_p$. N individual pulses (p) together form one smooth pulse (q) with a smooth pulse duration $T_Q$. Within one smooth pulse (q), the related individual pulses (p) follow each other with a smooth pulse repetition time $T_p$. The smooth pulses (q) are delivered to any location X (FIGS. 7, 8) on the target area 3 M times with a smooth pulse repetition time $T_s$. In other words, K is the total number of individual pulses (p) delivered to any location X (FIGS. 6A to 6H, 7) on the target area 3, wherein N is the individual pulse number of individual pulses (p) within one smooth pulse (q), and M is the smooth pulse number of smooth pulses (q) delivered to any location X (FIGS. 7, 8) on the target area 3. In FIG. 5, a sequence of K=9 pulses is shown, consisting of a sequence of N=3 individual pulses (p) within one single smooth pulse (q), wherein the smooth pulses (q) are repeated by M=3 times on the same location X (FIGS. 6A to 6H, 7). However, any other suitable values of the individual pulse number N and of the smooth pulse number M may be chosen as shown below.

Preferably, within one smooth pulse (q) a pulse sequence of N individual pulses (p) is provided, wherein individual pulses (p) follow each other with a pulse repetition time $T_p$ in a range from 0.01 s, inclusive, to 2.0 s, inclusive, in particular in a range from 0.01 s, inclusive, to 0.1 s, inclusive, and in particular in a range from 0.015 s, inclusive, to 0.03 s, inclusive, wherein a smooth pulse duration $T_Q$ of the smooth pulse (q) is in a range from 0.01 s, inclusive, to 10 s, inclusive. In a preferred embodiment, one smooth pulse (q) comprises of N=3 to 20 pulses (p), and the smooth pulse duration $T_Q$ is in a range from 0.1 s, inclusive, to 1.5 s, inclusive, and wherein preferably the smooth pulse (q) comprises N=5 pulses (p) and the smooth pulse duration $T_Q$ of 0.25 s.

Within one treatment procedure it may be sufficient to provide only one (M=1) smooth pulse (q) to any respective location X (FIGS. 7, 8) on the target area 3. However, it may be more energy efficient for a particular laser configuration to operate with relatively short pulse repetition times $T_p$. In such a case the duration of the irradiation of the target area 3 on the tissue during which the required cumulative fluence is delivered may be prolonged by delivering laser energy in M>1 multiple smooth pulses (q). Expediently, multiple smooth pulses (q) may follow each other with a multiple pulse repetition time $T_s$ in a range from 0.2 s, inclusive, to 2.0 s, inclusive, preferably in a range from 0.4 s, inclusive, to 1.6 s, inclusive, and in particular in a range from 0.6 sec to 1.1 s. In a preferred embodiment, the multiple pulse sequence comprises M=2 to 10 smooth pulses (q), and advantageously M=3 to 5 smooth pulses (q).

In a preferred embodiment, the cumulative fluence of the pulses of a single or multiple pulse sequence on the target area of the tissue is in a range from 1.0 J/cm², inclusive, to 30.0 J/cm², inclusive, preferably in a range from 3.0 J/m², inclusive, to 20.0 J/cm², inclusive, and is in particular at least approximately 9.0 J/cm². From a minimum cumulative fluence of 1.0 J/cm², a minimum of M=1 and a maximum of N=20 it follows, that the fluence of one individual pulse (p) may have a minimum down to 0.05 J/cm². Preferably the single pulse fluence delivered by the laser beam 2 to the respective location on the target area 3 is ≥0.15 J/cm², and even more preferably is >2.5 J/cm². And from a maximum cumulative fluence of 30.0 J/cm², a minimum of M=1 and a minimum of N=2 it follows, that the fluence of one individual pulse (p) may have a maximum of up to 15.0 J/cm². Preferably the single pulse fluence delivered by the laser beam 2 to the respective location on the target area 3 is ≤10.0 J/cm². Preferably, the single pulse fluence delivered by the laser beam 2 to the respective location on the target area 3 is in a range from 0.15 J/cm², inclusive, to 15.0 J/cm², inclusive, and even more preferably in a range from 2.5 J/cm², inclusive, to 10.0 J/cm², inclusive.

We have determined that with our method the superficial layer of the mucous tissue can be heated to temperatures in the range from 40 to 70 degrees Celsius, which is the temperature required to achieve reversible tissue damage leading to tissue shrinkage and new collagen generation. By controlling the thermal diffusion depth by using different pulsing schemes, the treatment focuses on the tissue just below its surface. It also allows for the system to be highly tunable to treatment indications and individual differences among patents.

There are two irradiation techniques, a "stamping" or an inventive "overlapping" irradiation technique, which can be used for heat pulsing using the inventive laser system 20 and treatment head 1.

When applying the stamping technique, the sequence of laser pulses (p) is delivered to a respective location on the target area 3 by having the control unit 22 configured to stop the rotation of the output element 5 and to start a laser pulse (p) sequence until at least all N pulses, or in certain embodiments all K pulses, have been delivered to any irradiation spot 24. For a more clear understanding of the stamping irradiation technique, a schematic view of the tissue heat diffusion when irradiated with the irradiation pattern according to FIG. 5 is shown in FIGS. 6A to 6H. Within FIGS. 6A to 6H eight irradiation steps A to H are exemplarily shown to demonstrate the stamping process. However, in reality more irradiation steps are performed following the same pattern principle.

In the beginning, the output element 5 is rotated until a specific start position is reached, in which a first irradiation spot 24 is about to be irradiated by the laser beam 2. The rotation of the output element 5 is then stopped, and an irradiation sequence according to FIG. 5 is applied. The rotation of the output element 5 is kept stopped until all pulses (p) in a sequence (an example for N=3 is shown) are delivered to a first irradiation spot 24 (FIG. 6, steps A to C). In other words, one smooth pulse (q) with three individual pulses (p) and with each a single pulse fluence $F_i$ is applied to the first irradiation spot 24. A first pulse (p) with a single pulse fluence $F_i$ is applied within first step A, according to which heat diffusion generates a heated volume $V_1$ within the mucosa tissue just below the tissue surface within the area of the irradiation spot 24. A second pulse (p) with a single pulse fluence $F_i$ is applied within second step B, according to which heat diffuses deeper into the tissue, thereby increasing the depth of the heated volume, which is indicated as $V_2$. A third pulse (p) with a single pulse fluence $F_i$ is applied within third step C, according to which heat diffuses even deeper into the tissue, thereby further increasing the depth of the heated volume being indicated as $V_3$. It can be desirable to continue next with step D as described infra. In such case a sequence of N pulses is applied to the irradiation spot 24. In other words, irradiation spot 24 receives one single, that is M=1 smooth pulse (q) consisting of N multiple, here three individual pulses (p). However, steps A to C may be repeated M times to apply M>1 smooth pulses (q) (FIG. 5), resulting in an irradiation of the first irradiation spot 24 by a total of K=N×M individual pulses (p) according to FIG. 5 with a cumulative fluence F, until a desired temperature and depth of the heated volume V is achieved.

The laser irradiation is then stopped and the output element 5 is rotated by an appropriate angle such that a second irradiation spot 24' is relocated relative to the first irradiation spot 24 in the helical relocation direction 31 by a distance equivalent to the second mean cross section extension $B_2$ (FIG. 6D). In consequence, the second irradiation spot 24', which is next to be irradiated, is located adjacent to the first, preceding irradiation spot 24 side by side without any considerable overlapping. Alternatively, there may be a gap left between a first irradiation spot 24, and a second irradiation spot 24' resulting in a spotted irradiation pattern in the helical direction 31. Again, the rotation of the output element 5 is then stopped and kept stopped, and an irradiation sequence of K=N×M pulses (p) according to FIG. 5 is applied to the second irradiation spot 24', as shown in steps D to F of FIGS. 6D to 6F, and as described above in connection with steps A to C of FIGS. 6A to 6C. An appropriate helical movement is performed again in order to enable delivery of a next pulse sequence to a third adjacent irradiation spot 24" (FIGS. 6G and 6H), and so on.

In an alternative second preferred "overlapping" irradiation technique, the control unit 22 is configured and operated to rotate the output element 5 at a continuous constant rotational speed ω, and to emit laser pulses (p) at a continuous constant repetition time $T_p$. To understand the inventive overlapping irradiation technique, reference is first made to FIG. 7. FIG. 7 shows a developed view of the target area 3 equivalent to the outer circumferential surface of the speculum 17 (FIG. 2) with the rotational angle φ over the longitudinal direction (x).

Upon rotating the output element 5 including its deflection means 7 by a rotation angle φ about the longitudinal axis 8 relative to the guide element 9, subsequent irradiation spots 24' are relocated relative to their preceding irradiation spots 24 on the helical path in a helical relocation direction 31 by the same rotation angle φ. The control unit 22 of the laser system 20 is configured and operated to adjust the preferably constant rotational speed ω of the output element 5 to the pulse repetition rate $T_p$ of the pulses (p) such that the target area 3 is irradiated in a helical pattern, while subsequent laser pulses (p) are continuously generated at the preferably constant pulse repletion rate $T_p$. The control unit 22 is further configured and operated to rotationally drive the laser output element 5 at a rotational speed co and to synchronize the rotational speed ω to the pulse repetition rate $T_p$ of the pulses (p) such, as shown in FIG. 7, that subsequent irradiation spots (24, 24') at least partially overlap each other in the helical relocation direction 31. The control unit 22 is configured and operated to irradiate a respective location on the target area 3, which is exemplarily marked as an X in FIG. 7, initially by the individual pulse number N of pulses (p), and to further adjust the rotational speed ω such that a second irradiation spot 24' is relocated relative to a first irradiation spot 24 by a fraction 1/N of the second mean spot cross section extension $B_2$ as measured in the helical relocation direction 31. In the present example the chosen individual pulse number N is three. In consequence, every irradiation spot 24 is relocated relative to its preceding irradiation spot 24 along the helical relocation direction 31 by one third of the mean spot cross section extension $B_2$, that is by $B_2/3$. However, any other suitable heat pumping or individual pulse number N may be chosen, wherein the individual pulse number N is preferably in a range from two to twenty, and in particular in a range from three to six. In consequence, subsequent irradiation spots (24, 24') overlap each other by $(N-1)B_2/N$, that is in the present example by $2 B_2/3$. In further consequence, every single reference point X on the target area 3 is irradiated by the same individual pulse number N of pulses (p), that is in the present example case by three pulses (p). The only exceptions are the negligible areas at the beginning and at end of the rotational scan.

For a more clear understanding of the overlapping irradiation technique in the helical relocation direction 31, a schematic view of the tissue heat diffusion when irradiated with the irradiation pattern according to FIG. 5 is shown in FIGS. 9A to 9H. As in FIGS. 6A to 6H, FIGS. 9A to 9H shows a schematic cross sectional view of the mucosa tissue 23 with heated volumes V within the mucosa tissue 23 just below the surface, as generated by pulses (p) of the laser beam 2. Again eight exemplary irradiation steps A to H are shown to demonstrate the entire irradiation pattern. Upon simultaneously viewing FIGS. 7 and 9A to 9H it becomes evident, that a first pulse (p) irradiating the first irradiation spot 24 with a single pulse fluence $F_i$ generates by heat diffusion a first heated volume $V_1$ within the area of the first irradiation spot 24, and with a certain depth extending down inside the mucosa tissue 23 from the tissue surface. In the second step B, the subsequent second pulse (p) irradiates the second, relocated irradiation spot 24' with a single pulse fluence $F_i$, which partially overlaps the preceding first irradiation spot 24. In the overlapping portion, heat diffuses deeper into the tissue, thereby generating a heated volume $V_2$ with increased depth. In the non-overlapping portion a first heated volume $V_1$ is generated by the second pulse (p) within the area of the second irradiation spot 24', analogously to first step A. In the subsequent third step C, the subsequent third pulse (p) irradiates the third, relocated irradiation spot 24" with a single pulse fluence $F_i$, which partially overlaps both preceding first and second irradiation spots (24, 24'). In the portion overlapping the second irradiation spot 24', heat diffuses deeper into the tissue, thereby generating a heated volume $V_2$ with increased depth, while in the portion overlapping the first irradiation spot 24, heat diffuses even deeper into the tissue, thereby generating a third heated volume $V_3$ with even more increased depth. Again as in second step B, in the non-overlapping portion a first heated volume $V_1$ is generated by the third pulse (p) within the area of the third irradiation spot 24", analogously to first step A.

For the present example of individual pulse number N being three and a helical irradiation spot relocation by one third of the mean spot cross section extension $B_2$, it occurs with the fourth pulse of fourth step D, that the fourth irradiation spot does not overlap with the first irradiation spot 24. In consequence, within the overlapping portions, all single pulse fluence $F_i$ sum up to a cumulative fluence F, which is in the present example the sum of three single pulse fluences $F_i$. In further consequence, the depth of the third heated volume $V_3$ does not increase anymore, while the width of third heated volume $V_3$ increases in the helical relocation direction 31, and while new adjacent first and second heated volume ($V_1$, $V_2$) are generated. Every single reference point X on the target area 3 along the helical irradiation path is irradiated by at least one smooth pulse (q) with the same individual pulse number N of three individual pulses (p). The same principle applies to any other combination of individual pulse numbers N and related helical irradiation spot relocations by 1/N of the mean spot cross section extension $B_2$. In any of such cases, every single reference point X on the target area 3 along the helical irradiation path is irradiated by at least one smooth pulse (q) with the same individual pulse number N of individual pulses (p).

The aforementioned relocation of the irradiation spots (24, 24') in the helical relocation direction 31 by a fraction 1/N of the second mean spot cross section extension $B_2$ is insofar a preferred example, in that the integer individual pulse numbers N and the integer fractions 1/N thereof lead to an exact evenly treated irradiation pattern, in which every single reference point X receives exact the same individual pulse number N of individual pulses (p). However, a non integer fraction of the second mean spot cross section extension $B_2$ for relocating the irradiation spots (24, 24') in the helical relocation direction 31 may be chosen as well in particular within the boundaries of 1/N of the above mentioned maximum individual pulse number N and of 1/N of the above mentioned minimum individual pulse number N. This will lead to a sufficient approximation to an evenly treated irradiation pattern.

Referring now back to FIG. 3, it can be seen that the first and second thread means (12, 13) together provide a thread pitch (b), as a consequence of which the entire output element 5 including its deflection means 7 perform an axial movement by the thread pitch (b) value upon rotating by a rotation angle φ=360°. After rotation by such rotation angle φ=360° the related irradiation spot 24''' is moved in the axial direction (x) relative to the preceding irradiation spot 24 by the value of the thread pitch (b).

Based on this, and referring again simultaneously to FIGS. 7 and 5, the overlapping technique may be restricted in the helical relocation direction 31 only. In such case, the thread pitch (b) (FIG. 3) is chosen to be at least approximately equal to the first mean cross section extension $B_1$ of the irradiation spots (24, 24', 24'', 24'''). In consequence and referring to the longitudinal movement direction (x), adjacent radiation spots (24, 24''') are located side by side without any gap along the entire helical path (FIG. 7), but also without any overlapping in the longitudinal direction (x). This again ensures, that every single reference point X on the target area 3 is irradiated by the same individual pulse number N of individual pulses (p). However, this also means, that every single reference point X on the target area 3 is irradiated by just one smooth pulse (q) (FIG. 5) with the predetermined individual pulse number N of individual pulses (p). In other words, the smooth pulse number M is one, and the total pulse number K is equal to the individual pulse number N.

However, the "overlapping" technique may be applied in the axial direction (x) as well. FIG. 8 shows a variant of FIG. 7 thereby demonstrating the additional axial overlapping. For achieving this, the thread pitch (b) is chosen such that a second irradiation spot 24'' is relocated relative to a first irradiation spot 24 by a fraction 1/M of the first mean spot cross section extension $B_1$. In other words, the thread pitch (b) and the first mean spot cross section extension B1 are adapted to each other such that the thread pitch (b) is 1/M of the first mean spot cross section extension $B_1$. In the present example of FIG. 8, the chosen smooth pulse number M is two. In consequence, the thread pitch (b) is ½ of the first mean spot cross section extension $B_1$, and every irradiation spot 24''' is relocated relative to its preceding irradiation spot 24 along the axial direction (x) by one half of the first mean spot cross section extension $B_1$, that is by $B_1/2$. However, any other suitable smooth pulse number M may be chosen, wherein the smooth pulse number is preferably in a range from two to ten and in particular from three to five. The multiple pulse repetition time $T_s$ is in this embodiment determined by the adjustable rotational speed ω, and is equal to the time required to perform a rotation by a rotation angle φ=360°. When using the overlapping technique in helical and axial direction, every single reference point X on the target area 3 is in consequence irradiated by the same individual pulse number N of pulses (p), and the same smooth pulse number M of smooth pulses (q). In FIG. 8, an example is shown for N=3 and M=2, and therefore for a total pulse number K of applied pulses (p) being K=3×2=6.

The aforementioned relocation of the irradiation spots (24, 24''') in the axial direction (x) by a fraction 1/M of the first mean spot cross section extension $B_1$ is insofar a preferred example, in that the integer smooth pulse numbers M and the integer fractions 1/M thereof lead to an exact evenly treated irradiation pattern, in which every single reference point X receives exact the same smooth pulse number M of smooth pulses (q). However, a non integer fraction of the first mean spot cross section extension $B_1$ for relocating the irradiation spots (24, 24''') in the axial direction (x) may be chosen as well in particular within the boundaries of 1/M of the above mentioned maximum smooth pulse number M and of 1/M of the above mentioned minimum smooth pulse number M. This will lead to a sufficient approximation to an evenly treated irradiation pattern.

With respect to the aforementioned "overlapping" technique it has to be appreciated that, although the laser system 20 generates pulses (p) at a constant pulse repetition rate or time $T_p$, every single reference point X on the target area 3 receives an irradiation by pulses (p) in a sequence as exemplarily shown in FIG. 5, that is by individual pulses (p) which may be grouped within individual smooth pulses (q) within the boundaries as described above.

Coming back to the stamping technique as of FIGS. 6A to 6H, the thread pitch (b) (FIG. 3) is chosen to be at least approximately equal to the first mean cross section extension $B_1$ of the irradiation spots (24, 24', 24'', 24'''), as described along with FIG. 7. In consequence and referring to the longitudinal movement direction (x), adjacent radiation spots (24, 24''') are located side by side without any gap along the entire helical path (FIG. 7). This again ensures, that every single reference point X on the target area 3 is irradiated by the same total pulse number N or K of individual pulses (p).

The aforementioned description of the relation between pulse repetition rate $T_p$, rotational speed ω, thread pitch (b) and mean irradiation spot extensions ($B_1$, $B_2$) applies exactly for the present case of a rectangular shaped irradiation spots (24, 24', 24'', 24'''). In case of deviating irradiation spot shapes equivalent mean cross section extensions ($B_1$, $B_2$) have to be derived for adjusting the pulse repetition rate $T_p$, rotational speed ω and the thread pitch (b) such that the reference points X on the target area 3 are a least approximately evenly irradiated to receive a laser irradiation energy dose equivalent to the above described irradiation by the heat pumping or total pulse number K=N×M of individual pulses (p).

A preferred first and/or second mean irradiation spot extension ($B_1$, $B_2$) is in the range from 0.1 mm, inclusive, to 15 mm, inclusive, in particular from 3 mm, inclusive, to 10 mm, inclusive. This range of extensions ($B_1$, $B_2$) corresponds approximately to the range of the radial dimensions of body cavity to be treated, and to the range of available laser spot sizes that can be delivered into a body cavity. When a conical optical element is chosen as a deflection means 7, ring shaped irradiation spots 24 are generated, with their second irradiation spot extension $B_2$ extending approximately over the circumference of the body cavity, being at least approximately equal to the circumference of the speculum or the a.m. other suitable radial distance means. The irradiation spots (24, 24', 24", 24''') have been described as being irradiated by a full cross section laser beam 2. However, as a further option within the invention, the laser system 20 may be configured to provide a dotted irradiation pattern within the irradiation spots (24, 24', 24", 24'''), as described in U.S. Pat. No. 8,709,057.

When the deflection means consists of multiple flat mirrors 14" of triangular shape, being arranged to form a pyramid, and the irradiation spot extension $B_2$ extends approximately over the multiple triangular flat mirrors of the pyramid, the incoming laser beam section 10 is spread in multiple spots distributed in the radial directions thereby producing a spotted irradiation pattern around the longitudinal axis 8. And when the deflection means 7 is a pair of opposite inclined flat mirrors 14' with non-reflecting front faces 33 in between, the incoming laser beam section 10 is spread in two spots distributed in two opposite radial directions thereby producing a two-spotted irradiation pattern around the longitudinal axis 8.

A preferred range of rotational speed ω corresponds to the preferred range of the multiple pulse repetition time $T_s$ following the rule $\omega=2\pi/T_s$. With the abovementioned preferred ranges for the multiple pulse repetition time $T_s$ the rotational speed co is therefore preferably in a range from 3.14 $\sec^{-1}$, inclusive, to 31.4 $\sec^{-1}$, inclusive, preferably from 3.93 $\sec^{-1}$, inclusive, to 15.71 $\sec^{-1}$, inclusive and in particular from 5.71 $\sec^{-1}$, inclusive, to 10.47 $\sec^{-1}$, inclusive. Similarly a preferred range of the thread pitch (b) corresponds to the preferred range of the smooth pulse number M, and of the first irradiation spot extension $B_1$, following the rule $b=B_1/M$. With the a.m. preferred ranges for the smooth pulse number M and the first irradiation spot extension $B_1$ the preferred range of the thread pitch (b) is therefore from 3 mm/10=0.3 mm, inclusive, to 15.0 mm/1=15 mm, inclusive, in particular from 3 mm/5=0.6 mm, inclusive, to 15.0 mm/2=7.5 mm, inclusive, and even more preferably from 3 mm/5=0.6 mm, inclusive, to 10.0 mm/3=3.33 mm, inclusive.

The control unit 22 and the laser treatment head 1 are further configured and operated to deliver a certain cumulative fluence F to the target area 3. In particular, the energy of each single individual pulse and the optical system to generate a specific area of each individual irradiation spot (24, 24', 24", 24''') are adjusted both to each other and the chosen total pulse number N or K such that the respective reference locations X on the target area 3 receive a cumulative fluence F by the laser beam 2 being in a range in a range from 2.0 J/cm², inclusive, to 30.0 J/cm², inclusive, preferably in a range from 3.0 J/cm², inclusive, to 20.0 J/cm², inclusive, and is in particular at least approximately 9.0 J/cm². From a minimum cumulative fluence of 1.0 J/cm², a minimum of M=1 and a maximum of N=20 it follows, that the fluence of one individual pulse (p) may have a minimum down to 0.05 J/cm². Preferably the single pulse fluence delivered by the laser beam 2 to the respective location on the target area 3 is ≥0.15 J/cm², and even more preferably is >2.5 J/cm². And from a maximum cumulative fluence of 30.0 J/cm², a minimum of M=1 and a minimum of N=2 it follows, that the fluence of one individual pulse (p) may have a maximum of up to 15.0 J/cm². Preferably the single pulse fluence delivered by the laser beam 2 to the respective location on the target area 3 is ≤10.0 J/cm². Preferably, the single pulse fluence delivered by the laser beam 2 to the respective location on the target area 3 is in a range from 0.15 J/cm², inclusive, to 15.0 J/cm², inclusive, and even more preferably in a range from 2.5 J/cm², inclusive, to 10.0 J/cm², inclusive.

Thereby the target area 3 is irradiated by subsequent pulses (p) in a helical pattern of irradiation spots (24, 24', 24", 24''') over at least a section of the circumference of the body cavity 4, thereby heating the mucosa tissue within the target area 3 to a predetermined temperature. In particular, the mucosa tissue is thereby heated to a temperature in a range from 40° C. to 70° C., and preferably from 42° C. to 65° C. which is a non-ablative heating. However, within the scope of the present invention a slightly higher heating (above the boiling temperature of water) may be achieved with a slight amount of ablation effects. It is important to note, however, that when the tissue's interstitial water is heated above the boiling temperature, micro-explosive ejection of the over-heated tissue occurs, effectively leaving behind only the tissue with an average bulk temperature below 70° C.

Further, the control unit 22 and the laser treatment head 1 may be configured and operated not to deliver irradiation to certain regions of the area 3 of the cavity 4. For example, laser beam generation may be stopped whenever the irradiation spot 24 on the target area 3 is located approximately beneath the urethra.

In certain embodiments, the laser source with a water transmitted wavelength may be used. In such embodiment, the pulse numbers, K, N and M are preferably small, in particular preferably equal to one.

Further, a combined laser wavelength treatment may be performed using two laser sources (21, 21'), one with a "water transmitted" wavelength, and the other with a "water absorbed" wavelength whereas the bulk tissue is pre or post heated with a water transmitted wavelength transmitted by laser source 21, and the more superficially lying tissue is heated by a water absorbed wavelength transmitted by laser source 21', both heat treatments performed according to the inventive methods described above. The combined heating may be performed with a water transmitted wavelength being delivered simultaneously with the water absorbed wavelength. Alternatively, the laser irradiations may be performed in a fast alternating sequence of both laser wavelengths.

Additionally, an IR temperature sensor may be included to measure the temperature of the tissue surface, and then used as a feedback to achieve uniform and/or optimal heating of the tissue.

In one preferred embodiment, the cylindrical speculum 17 is made out of an optical material transmitting at least 70% of laser radiation, and preferably at least 90% of laser radiation. Alternatively, the speculum 17 may be replaced by a wire mesh or other suitable radial distance means. The external radius of the speculum 17 or other radial distance means is in a range from 15 mm, inclusive, to 35 mm, inclusive, and preferably in a range from 20 mm, inclusive, to 30 mm, inclusive. The rotational speed is in a range from 4.0 $\sec^{-1}$, inclusive, to 15.0 $\sec^{-1}$, inclusive, and is preferably in a range from 6.0 $\sec^{-1}$, inclusive, to 10.0 $\sec^{-1}$, inclusive. The preferred ranges of the rotational speed ω correspond to preferred ranges of the multiple pulse repetition time $T_s$ being in a range from 1.57 s, inclusive, to 0.42 s, inclusive, and preferably in a range from 1.05 s, inclusive, to 0.63 s, inclusive, The thread pitch (b) is in a range from 0.5 mm, inclusive, to 2 mm, inclusive, preferably in a range from 0.75 mm, inclusive, to 1.5 mm, inclusive. When "overlapping" irradiation technique is used, individual laser pulses (p) are generated with a constant repetition time $T_p$ in a range from 0.01 s, inclusive, to 0.1 s, inclusive, and preferably in a range from 0.015 s, inclusive, to 0.03 s, inclusive. The energy of individual pulses (p) is in a range from 30 mJ, inclusive, to 1000 mJ, inclusive, and is preferably in a range from 100 mJ, inclusive, to 300 mJ, inclusive. When the deflection means 7 consists of a flat mirror, the mean irradiation spot extensions ($B_1$, $B_2$) are in a range from 4 mm, inclusive, to 15 mm, inclusive, and are preferably in a range from 7 mm, inclusive, to 10 mm, inclusive. When the deflection means 7 consists of a conical mirror, the mean irradiation spot extension $B_2$ extends across the speculum's external circumference, and the spot extension $B_1$ is in a range from 4 mm, inclusive, to 15 mm, inclusive, and is preferably in a range from 7 mm, inclusive, to 10 mm, inclusive.

Figure 11:
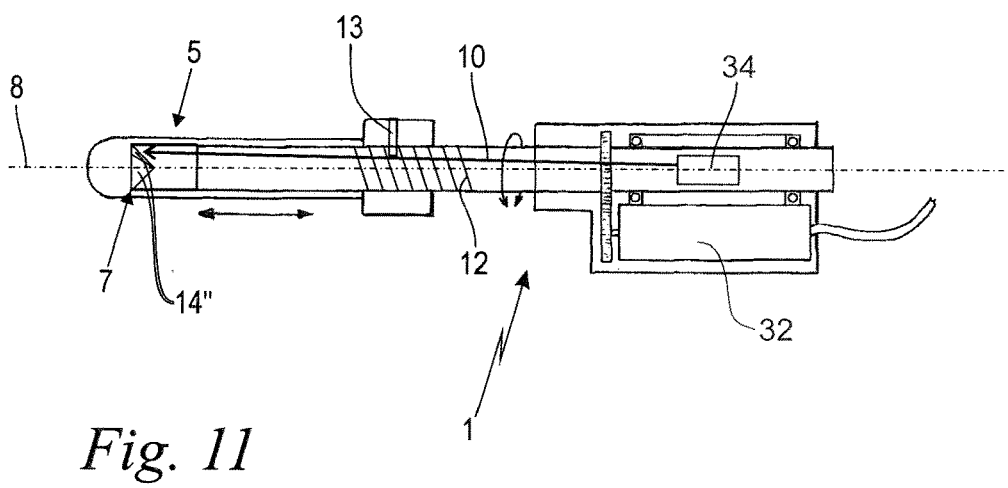
FIG. 11 illustrates in a schematic view another variant of the laser treatment head according to FIG. 2 having a scanner and a pyramidal shaped mirror; and, FIG. 12 illustrates in a schematic view a further variant of the laser treatment head according to FIG. 2 having scanner and a pair of opposite inclined mirrors.
Figure 12:
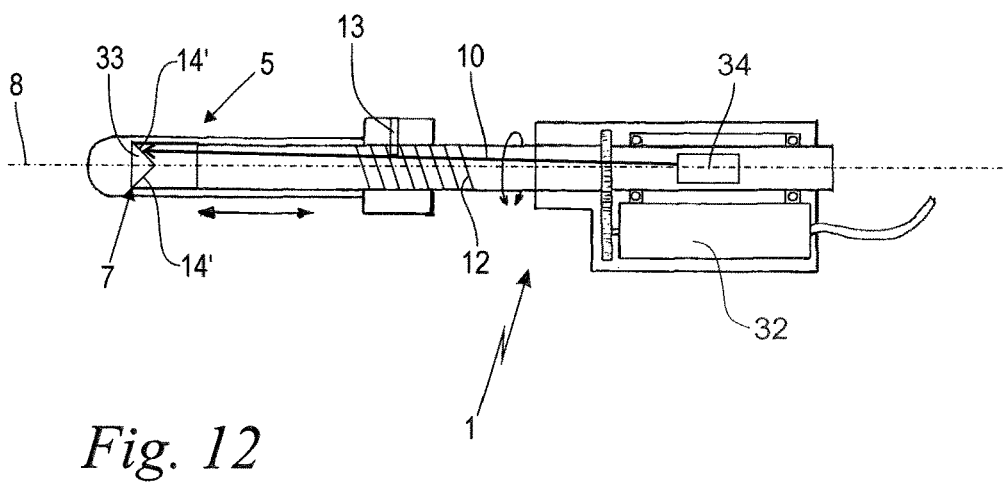

FIGS. 10 to 12 each show in a schematic view a variant of the laser treatment head 1 according to FIG. 2, each having a schematically indicated scanner 34. During operation the deflection means 7 are scanned with the incoming laser beam section 10 of the laser beam 2 by means of the scanner 34. In the embodiment according to FIG. 10 the deflection means 7 are a cone shaped mirror 14''', the apex of which is facing the incoming beam section 10. The half opening angle of the cone is 45°. In any plane as defined by the longitudinal axis 8 and an arbitrary radial direction thereto, the angle between the reflecting surface of the cone shaped mirror 14''' and the longitudinal axis 8 is therefore 45° analogue to FIG. 3. In operation, the reflecting conical surface of the cone shaped mirror 14''' is scanned with the incoming bean section 10 in a circular pattern around the longitudinal axis 8, thereby generating a controlled circular feed of the output beam section 11 (FIG. 3). The scanning is synchronized to the motor drive speed of the laser treatment head 1 and to the generation of the pulses (p) such that in connection with the combined rotational and axial movement of the output element 5, as described along with FIGS. 1 to 9H, a helical irradiation pattern according to FIGS. 5 to 9H is achieved.

In the embodiment of FIG. 11, the cone shaped mirror 14''' of FIG. 10 is replaced by multiple flat mirrors 14'' of triangular shape, being arranged to form a pyramid. In all other details, the laser treatment head 1 of FIG. 11 is identical to the laser treatment head 1 of FIG. 10. When scanned with the laser beam, the flat mirrors 14'' reflect the incoming laser beam section without significant optical distortion and defocusing. The same applies to the embodiment of FIG. 12, wherein the deflection means 7 is a pair of opposite inclined flat mirrors 14' with non-reflecting front faces 33 in between. In the particular case of FIG. 12 the scanning procedure may be reduced to alternatively irradiating one of the two mirrors 14', while a circular feed is generated by the rotational movement of the output element 5 including its two flat mirrors 14'. In all other aspects, unless not explicitly mentioned in the opposite, the physical embodiments and process steps of FIGS. 1 to 12 are identical to one another.

It is understood that the foregoing description is that of the preferred embodiments of the invention and that various changes and modifications may be made thereto without departing from the spirit and scope of the invention as defined in the appended claims.

What is claimed is:

1. A laser treatment head for guiding a laser beam to a target area within a body cavity, the laser treatment head comprising:
   a laser output element defining and extending along a longitudinal axis;
   said laser output element including a carrier member and being configured to output a laser beam;
   a guide element for said laser output element configured to have an incoming, substantially coaxial laser beam section of said laser beam pass therethrough during operation;
   said laser output element further including a deflection element configured to deflect said incoming, substantially coaxial laser beam section into a substantially radial output laser beam section;
   said deflection element being fixed to said carrier member;
   said laser output element including said deflection element being configured to be rotatable relative to said guide element about said longitudinal axis;
   said carrier member including a first thread element;
   said guide element including a second thread element; and,
   said first thread element and said second thread element being configured to mutually engage so as to cause said deflection element to perform a combined axial and rotational movement relative to said guide element in response to a rotational movement of said laser output element relative to said guide element.

2. The laser treatment head of claim 1, wherein:
   said deflection element is a mirror having a reflecting surface; and,
   said mirror is fixed to said carrier member such that said reflecting surface and said longitudinal axis of said laser output element conjointly define an angle ($\alpha$) lying in a range of 30° to 60°.

3. The laser treatment head of claim 2, wherein said deflection element is one of a single flat mirror, a pair of oppositely inclined mirrors, a multiplicity of flat mirrors arranged to form a pyramid and a cone shaped mirror.

4. The laser treatment head of claim 2 further comprising:
   a scanner configured to scan said mirror with said incoming laser beam section of said laser beam.

5. The laser treatment head of claim 1 further comprising:
   a radial distance element attached to said guide element and arranged so as to cover said laser output element; and,
   said radial distance element being at least partially transmissive with respect to said laser beam.

6. The laser treatment head of claim 1, wherein:
   the target area has a first mean cross section extension ($B_1$) measured in an axial direction (x) parallel to said longitudinal axis;
   the laser treatment head is configured to irradiate irradiation spots on the target area;
   said first and second threaded sections conjointly define a threaded pitch (b); and,
   said thread pitch (b) is at least approximately equal to the first mean cross section ($B_1$) of said irradiation spots or is a fraction thereof.

7. The laser treatment head of claim 1 further comprising:
   a motor configured to rotationally drive said laser output element so as to generate said combined axial and rotational movement of said laser output element relative to said guide element as a motorized combined axial and rotational movement.

8. The laser treatment head of claim 7, wherein said motor is a single motor and said guide element is fixed in position within said laser treatment head.

9. The laser treatment head of claim 1, wherein said combined axial and rotational movement causes said deflection element to provide a helical irradiation pattern within the body cavity of a patient.

10. A laser system for thermal treatment of mucosa tissue within a target area in a body cavity, the laser system comprising:
- a laser source configured to generate a laser beam;
- a laser treatment head for guiding said laser beam to a target area within a body cavity;
- said laser treatment head including a laser output element and a guide element;
- said laser output element defining and extending along a longitudinal axis;
- said laser output element including a carrier member;
- said guide element for said laser output element configured to have an incoming, substantially coaxial laser beam section of said laser beam pass therethrough during operation;
- said laser output element further including a deflection element configured to deflect said incoming, substantially coaxial laser beam section into a substantially radial output laser beam section;
- said deflection element being fixed to said carrier member;
- said laser output element including said deflection element being configured to be rotatable relative to said guide element about said longitudinal axis;
- said carrier member including a first thread element;
- said guide element including a second thread element;
- said first thread element and said second thread element being configured to mutually engage so as to cause said deflection element to perform a combined axial and rotational movement relative to said guide element in response to a rotational movement of said laser output element relative to said guide element;
- a motor configured to rotationally drive said laser output element so as to generate said combined axial and rotational movement of said laser output element relative to said guide element as a motorized combined axial and rotational movement;
- a control unit configured to control the drive speed of said motor and to control said laser source so as to generate said laser beam in individual pulses (p);
- said control unit and said laser treatment head being configured such that the target area is irradiated by said individual pulses (p) in a helical pattern of irradiation spots over at least a section of the circumference of the body cavity; and,
- said control unit is further configured such that reference locations (X) on the target area are irradiated by an individual pulse number (N) of subsequent pulses (p) thereby heating the mucosa tissue within the target area to a predetermined temperature.

11. The laser system of claim 10 further comprising:
- a scanner;
- said deflection element is a mirror;
- said control unit is further configured to scan said mirror with said incoming laser beam section of said laser beam via said scanner being synchronized to the drive speed of said laser treatment head and the generation of said pulses (p).

12. The laser system of claim 10, wherein said individual pulse number (N) lies in a range from 3 to 20.

13. The laser system of claim 12, wherein subsequent individual pulses (p) follow each other at a pulse repetition rate ($T_p$) lying in a range of 0.01 seconds to 2.0 seconds.

14. The laser system of claim 10, wherein:
- the laser system including its control unit is configured to irradiate a reference location (X) of the target area by a smooth pulse number (M) of subsequent smooth pulses (q);
- said smooth pulses (q) consist of said individual pulse number (N) of subsequent pulses (p); and,
- said smooth pulse number (M) lies in a range from 2 to 10.

15. The laser system of claim 10, wherein said control unit is configured such that said individual pulse number (N) of subsequent pulses (p) follow each other at a smooth pulse repetition time (TS) lying in a range from 0.2 seconds to 2.0 seconds.

16. The laser system of claim 10, wherein said control unit is configured such that said individual pulse number (N) of subsequent pulses (p), while the motor of the said laser treatment head and thus the combined rotational and axial movement of the laser output element is stopped.

17. The laser system of claim 10, wherein said control unit is configured such that said laser output element is continuously moved in a combined rotational and axial movement while subsequent laser pulses (p) are continuously generated at a pulse repetition rate ($T_p$).

18. The laser system of claim 17, wherein:
- said control unit and said laser treatment head are configured such that subsequent irradiation spots related to subsequent laser pulses (p) are generated along a helical path in a helical relocation direction, each irradiation spot having a second mean cross section extension ($B_2$) measured in said helical relocation direction; and,
- said control unit is further configured to synchronize the rotational speed of said laser output element to the pulse repetition rate ($T_p$) of said pulses (p) such that subsequent irradiation spots at least partially overlap each other.

19. The laser system of claim 18, wherein:
- said control unit is configured to irradiate a reference location (X) on the target area by the individual pulse number (N) of pulses (p) upon adjusting the rotational speed ($\omega$) and the pulse repetition rate ($T_p$) to each other such that a second irradiation spot is relocated relative to a first irradiation spot by a fraction 1/N of the second mean cross section extension ($B_2$).

20. The laser system of claim 18, wherein said control unit is configured to irradiate a respective irradiation spot on the target area having—measured in an axial direction (x) parallel to the longitudinal axis—a first mean cross section extension ($B_1$), wherein the thread pitch (b) of the laser treatment head is at least approximately equal to said first mean cross section extension ($B_1$) of said irradiation spot.

21. The laser system of claim 18, wherein said control unit is configured to irradiate a respective reference location (X) on the target area by a smooth pulse number (M) of subsequent smooth pulses (q) upon adjusting the first mean cross section extension ($B_1$) of the respective irradiation spots to the thread pitch (b) of the laser treatment head such that the thread pitch (b) is at least approximately equal to a smooth pulse fraction 1/M of the second mean cross section extension ($B_1$).

22. The laser system of claim 10, wherein said control unit and said laser treatment head are configured to deliver a cumulative fluence (F) by said laser beam to the respective location on the target area being in a range from 1.0 J/cm², inclusive, to 30.0 J/cm².

23. The laser system of claim 10, wherein said control unit and the laser treatment head are configured to deliver a single pulse fluence ($F_i$) by the laser beam to the respective location on the target area being ≥0.15 J/cm².

24. The laser system of claim 10, wherein the laser source is a laser generating a laser beam with a water absorbed wavelength (λ) lying in a range from above 1.9 µm to 11.0 µm inclusive.

25. The laser system of claim 10, wherein the laser system is configured to heat the mucosa tissue to a temperature lying in a range from 50° C. to 70° C.

26. A method for treating muscosa tissue within a target area in a body cavity using a laser system including a laser system for thermal treatment of mucosa tissue within a target area in a body cavity, the laser system comprising: a laser source configured to generate a laser beam; a laser treatment head for guiding said laser beam to a target area within a body cavity; said laser treatment head including a laser output element and a guide element; said laser output element defining and extending along a longitudinal axis; said laser output element including a carrier member; said guide element for said laser output element configured to have an incoming, substantially coaxial laser beam section of said laser beam pass therethrough during operation; said laser output element further including a deflection element configured to deflect said incoming, substantially coaxial laser beam section into a substantially radial output laser beam section; said deflection element being fixed to said carrier member; said laser output element including said deflection element being configured to be rotatable relative to said guide element about said longitudinal axis; said carrier member including a first thread element; said guide element including a second thread element; said first thread element and said second thread element being configured to mutually engage so as to cause said deflection element to perform a combined axial and rotational movement relative to said guide element in response to a rotational movement of said laser output element relative to said guide element; a motor configured to rotationally drive said laser output element so as to generate said combined axial and rotational movement of said laser output element relative to said guide element as a motorized combined axial and rotational movement; a control unit configured to control the drive speed of said motor and to control said laser source so as to generate said laser beam in individual pulses (p); said control unit and said laser treatment head being configured such that the target area is irradiated by said individual pulses (p) in a helical pattern of irradiation spots over at least a section of the circumference of the body cavity; and, said control unit is further configured such that reference locations (X) on the target area are irradiated by an individual pulse number (N) of subsequent pulses (p) thereby heating the mucosa tissue within the target area to a predetermined temperature, the method comprising the steps of:
inserting a treatment portion of the laser treatment head into the body cavity;
rotationally driving the laser output element of the laser treatment head relative to the guide element while keeping the guide element in a fixed position relative to the body cavity, thereby moving the laser output element in a combined rotational and axial movement;
generating a laser beam in individual pulses (p) via the laser treatment head under control of the control unit;
guiding the laser beam to the target area via the laser treatment head, wherein the target area is irradiated by individual pulses (p) in a helical pattern of irradiation spots over at least a section of the circumference of the body cavity; and,
irradiating reference locations (X) on the target area by an individual pulse number (N) of subsequent pulses (p), thereby heating the muscosa tissue within the target area to a predetermined temperature.

27. The method of claim 26, wherein the laser system further has a scanner and the deflection element is a mirror, the method further comprising the step of:
scanning the mirror with the incoming laser beam section of the laser beam via the scanner being synchronized to the motor drive speed of the laser treatment head and the generation of the pulses (p).

28. The method of claim 26 further comprising the subsequent step of:
subsequently irradiating reference locations (X) on the target area by an individual pulse number (N) lying in a range from 3 to 20.

29. The method of claim 28, wherein subsequent individual pulses (p) follow each other at a pulse repetition rate ($T_p$) lying in a range from 0.01 seconds to 2.0 seconds.

30. The method of claim 26, wherein a reference location (X) on the target area is irradiated by a smooth pulse number (M) of subsequent smooth pulses (q), wherein each smooth pulse (q) consists of the individual pulse number (N) of subsequent pulses (p); and, the smooth pulse number (M) lies in a range from 2 to 10.

31. The method of claim 30, wherein subsequent smooth pulses (q) follow each other at a smooth pulse repetition time ($T_s$) lying in a range from 0.2 seconds to 2.0 seconds.

32. The method of claim 26, further comprising the steps of:
rotationally driving the laser output element, thereby moving the laser output element in a combined rotational and axial movement to a starting position;
stopping the laser output element movement;
irradiating a first irradiation spot by the individual pulse number (N) of subsequent pulses (p), and in particular by the smooth pulse number (M) of subsequent smooth pulses (q), while the motor of the laser treatment head and thus the combined rotational and axial movement of the laser output element is stopped;
after irradiating the first irradiation spot, rotationally driving the laser output element, thereby moving the laser output element to a subsequent position for irradiating a second irradiation spot adjacent to the first irradiation spot;
irradiating the second irradiation spot by the individual pulse number (N) of subsequent pulses (p), and in particular by the smooth pulse number (M) of subsequent smooth pulses (q), while the motor of the laser treatment head and thus the combined rotational and axial movement of the laser output element is stopped; and,
continuing with the alternating irradiation and movement, until the target area is irradiated to the desired extent.

33. The method of claim 26, wherein the laser output element is continuously moved in a combined rotational and axial movement preferably at a constant rotational speed (c), while subsequent laser pulses (p) are continuously generated at a preferably constant pulse repetition rate ($T_p$), thereby irradiating the target area with subsequent irradiation spots along a helical path in a helical relocation direction.

34. The method of claim 33, wherein subsequent irradiation spots related to the subsequent laser pulses (p) are adjusted to each have—measured in the helical relocation direction—a second mean cross section extension ($B_2$), and wherein said rotational speed (ω) is synchronized to the pulse repetition rate ($T_p$) of the pulses (p) such that subsequent irradiation spots at least partially overlap each other.

35. The method of claim 34, wherein the rotational speed (co) and the pulse repetition rate ($T_p$) are adjusted to each other for irradiating a respective reference location (X) on the target area by the individual pulse number (N) of pulses (p) such that a second irradiation spot is relocated relative to a first irradiation spot by an fraction 1/N of the second mean cross section extension ($B_2$).

36. The method of claim 34, wherein the laser treatment head has a thread pitch (b), and wherein subsequent irradiation spots related to the subsequent laser pulses (p) are adjusted to each have—measured in an axial direction (x) parallel to the longitudinal axis—a first mean cross section extension ($B_1$) being at least approximately equal to the thread pitch (b) of the laser treatment head, thereby—after rotating the output element by a rotational angle ($\varphi$) of 360°—irradiating an irradiation spot being adjacent to a preceding irradiation spot in the axial direction (x).

37. The method of claim 34, wherein the laser treatment head has a thread pitch (b), and wherein subsequent irradiation spots related to the subsequent laser pulses (p) are adjusted to each have—measured in an axial direction (x) parallel to the longitudinal axis—a first mean cross section extension ($B_1$) such, that the thread pitch (b) is at least approximately equal to a smooth pulse fraction 1/M of the second mean cross section extension ($B_1$), thereby—after rotating the output element by a rotational angle ($\varphi$) of 360°—irradiating an irradiation spot overlapping a preceding irradiation spot in the axial direction (x), and thereby irradiating a respective reference location (X) on the target area by the smooth pulse number (M) of subsequent smooth pulses (q).

38. The method of claim 26, wherein a cumulative fluence (F) delivered by the laser beam to the respective location on the target area is in a range from 1.0 J/cm$^2$, inclusive, to 30.0 J/cm$^2$.

39. The method of claim 26, wherein a single pulse fluence ($F_i$) delivered by the laser beam to the respective location on the target area is $\geq 0.15$ J/cm$^2$.

40. The method of claim 26, wherein the mucosa tissue is heated to a temperature in a range from 50° C. to 70° C.

41. The laser system of claim 10, further comprising an optical delivery system connecting said laser source to said laser treatment head; and, said optical delivery system including an articulated arm for connecting said laser source to said laser treatment head.

42. The laser system of claim 10, further comprising an optical delivery system connecting said laser source to said laser treatment head; and, said optical delivery system including an elongated fiber connecting said laser source to said laser treatment head.

* * * * *

UNITED STATES PATENT AND TRADEMARK OFFICE
CERTIFICATE OF CORRECTION

PATENT NO. : 10,080,908 B2
APPLICATION NO. : 14/743917
DATED : September 25, 2018
INVENTOR(S) : M. Kazic et al.

Page 1 of 1

It is certified that error appears in the above-identified patent and that said Letters Patent is hereby corrected as shown below:

In Column 4:
Line 5: delete "A = 2.9 μm" and substitute -- $\lambda$ = 2.9 μm -- therefor.

In Column 15:
Line 44: delete "co" and substitute -- ω -- therefor.

In Column 19:
Line 24: delete "co" and substitute -- ω -- therefor.

In Column 25:
Line 11: delete "muscosa" and substitute -- mucosa -- therefor.

In Column 26:
Line 3: delete "muscosa" and substitute -- mucosa -- therefor.
Line 58: delete "(c)" and substitute -- (ω) -- therefor.

In Column 27:
Line 4: delete "(co)" and substitute -- (ω) -- therefor.

Signed and Sealed this
Sixteenth Day of April, 2019

Andrei Iancu
*Director of the United States Patent and Trademark Office*